(12) United States Patent
Larson et al.

(10) Patent No.: US 11,834,492 B2
(45) Date of Patent: Dec. 5, 2023

(54) HUMAN IL-10 RECEPTOR ALPHA FUSION PROTEINS

(71) Applicant: EpicentRx, Inc., La Jolla, CA (US)

(72) Inventors: Christopher Larson, San Diego, CA (US); Tony R. Reid, San Diego, CA (US); Bryan T. Oronsky, Los Altos Hills, CA (US)

(73) Assignee: EPICENTRX, INC., La Jolla, CA (US)

( * ) Notice: Subject to any disclaimer, the term of this patent is extended or adjusted under 35 U.S.C. 154(b) by 86 days.

(21) Appl. No.: 16/651,079

(22) PCT Filed: Sep. 27, 2018

(86) PCT No.: PCT/US2018/053197
§ 371 (c)(1),
(2) Date: Mar. 26, 2020

(87) PCT Pub. No.: WO2019/067770
PCT Pub. Date: Apr. 4, 2019

(65) Prior Publication Data
US 2020/0223901 A1  Jul. 16, 2020

Related U.S. Application Data

(60) Provisional application No. 62/564,145, filed on Sep. 27, 2017.

(51) Int. Cl.
| | | |
|---|---|---|
| *C07K 14/715* | (2006.01) | |
| *A61P 35/00* | (2006.01) | |
| *C07K 14/54* | (2006.01) | |
| *C12N 15/62* | (2006.01) | |
| *A61K 38/00* | (2006.01) | |

(52) U.S. Cl.
CPC .......... *C07K 14/7155* (2013.01); *A61P 35/00* (2018.01); *C07K 14/5428* (2013.01); *C12N 15/62* (2013.01); *A61K 38/00* (2013.01); *C07K 2319/03* (2013.01); *C07K 2319/30* (2013.01); *C07K 2319/50* (2013.01)

(58) Field of Classification Search
CPC combination set(s) only.
See application file for complete search history.

(56) References Cited

U.S. PATENT DOCUMENTS

| | | | |
|---|---|---|---|
| 4,816,567 | A | 3/1989 | Cabilly et al. |
| 4,946,778 | A | 8/1990 | Ladner et al. |
| 4,980,286 | A | 12/1990 | Morqan et al. |
| 5,482,858 | A | 1/1996 | Huston et al. |
| 5,525,491 | A | 6/1996 | Huston et al. |
| 6,472,179 | B2 | 10/2002 | Stahl et al. |
| 7,083,950 | B2 | 8/2006 | Stahl et al. |
| 9,073,980 | B2 | 7/2015 | Reid et al. |
| 10,906,957 | B2 | 2/2021 | Larson et al. |
| 2002/0004037 | A1 | 1/2002 | Koteliansky et al. |
| 2003/0125251 | A1 | 7/2003 | Wakefield et al. |
| 2005/0042220 | A1 | 2/2005 | Li et al. |
| 2007/0184052 | A1 | 8/2007 | Lin et al. |
| 2009/0111146 | A1 | 4/2009 | Ohtsuka et al. |
| 2009/0175819 | A1* | 7/2009 | Priest ...................... A61P 37/00 435/7.1 |
| 2010/0204104 | A1 | 8/2010 | Qiu et al. |
| 2015/0225483 | A1 | 8/2015 | Lo |
| 2018/0134766 | A1 | 5/2018 | Larson et al. |
| 2021/0139560 | A1 | 5/2021 | Reid et al. |

FOREIGN PATENT DOCUMENTS

| | | |
|---|---|---|
| CN | 1257545 A | 6/2000 |
| CN | 1382158 A | 11/2002 |
| CN | 105934249 A | 9/2016 |
| EP | 2326670 A1 | 6/2011 |
| JP | 2001515360 A | 9/2001 |
| JP | 2008106076 A | 5/2008 |
| JP | 2011526794 A | 10/2011 |
| JP | 2012519014 A | 8/2012 |
| JP | 2013521311 A | 6/2013 |
| JP | 2015516815 A | 6/2015 |
| JP | 2016512508 A | 4/2016 |
| KR | 1020010006534 A | 1/2001 |
| WO | WO-1993010151 A1 | 5/1993 |
| WO | WO-1996011213 A1 | 4/1996 |
| WO | WO-1997006826 A1 | 2/1997 |
| WO | WO-1998027216 A1 | 6/1998 |
| WO | WO-1998040498 A2 | 9/1998 |
| WO | WO-1998048024 A1 | 10/1998 |

(Continued)

OTHER PUBLICATIONS

Li et al. Temporal associations between interleukin 22 and the extracellular domains of IL-22R and IL-10R2. Internat. Immunopharcol., 4, 693-708, 2004. (Year: 2004).*
Terai et al., Human interleukin 10 receptor 1/IgG1-Fc fusion proteins: immunoadhesins for human IL-10 with therapeutic potential. Cancer Immunol.Immunother. 58, 1307-1317, 2009. (Year: 2009).*
Alignment of Seq ID Nos. 12 and 33. (Year: 2023).*
Chung et al., (2002). "Catheter-based adenovirus-mediated local intravascular gene delivery of a soluble TGF-beta type II receptor using an Infiltrator in porcine coronary arteries: efficacy and complications," Exp. Molecular Med., 34(4):299-307.
Connolly et al. (2012) "Complexities of TGF-13 targeted cancer therapy," Int. J. Biol. Sci., 8(7):964-78.

(Continued)

Primary Examiner — Elly-Gerald Stoica
(74) Attorney, Agent, or Firm — Morrison & Foerster LLP

(57) ABSTRACT

Provided is a fusion protein, e.g., a cytokine receptor fusion protein, e.g., an IL-10 trap, with a novel linker sequence to permit the fusion protein to functionally optimally, e.g., to permit a cytokine receptor portion of a cytokine receptor fusion protein to bind optimally to its target cytokine. The fusion protein, or an expression vector encoding for the fusion proteins, can be used to treat cell proliferative diseases and disorders, including certain forms of cancer and inflammatory disorders.

11 Claims, 3 Drawing Sheets
Specification includes a Sequence Listing.

(56) References Cited

FOREIGN PATENT DOCUMENTS

| WO | WO-2001003737 A1 | | 1/2001 |
|----|---|---|---|
| WO | WO-2001010912 A1 | | 2/2001 |
| WO | WO-2003066002 | * | 8/2003 |
| WO | WO-2005005638 A2 | | 1/2005 |
| WO | WO-2005024027 A1 | | 3/2005 |
| WO | WO-2006084327 A1 | * | 8/2006 |
| WO | WO-2008024188 A2 | | 2/2008 |
| WO | WO-2008147143 A2 | | 12/2008 |
| WO | WO-2008157367 A1 | | 12/2008 |
| WO | WO-2009154995 A2 | * | 12/2009 |
| WO | WO-2010003118 A1 | | 1/2010 |
| WO | WO-2010031168 A1 | | 3/2010 |
| WO | WO-2011109789 A2 | | 9/2011 |
| WO | WO-2013164694 A1 | | 11/2013 |
| WO | WO-2014164427 A1 | | 10/2014 |
| WO | WO-2015027082 A1 | | 2/2015 |
| WO | WO-2015077540 A2 | | 5/2015 |
| WO | WO-2016100788 A1 | | 6/2016 |
| WO | WO-2016174575 A1 | * | 11/2016 |
| WO | WO-2017037634 A1 | | 3/2017 |
| WO | WO-2018126282 A1 | * | 7/2018 |

OTHER PUBLICATIONS

Dumoutier et al., (2003). "Cloning of a new type II cytokine receptor activating signal transducer and activator of transcription (STAT)1, STAT2 and STAT3," Biochemical Journal, 370:391-396.
Extended European Search Report for European Patent Application No. 18862997.6 dated Aug. 13, 2021, 8 pages.
Fiorentino et al., (1989). "Two types of mouse T helper cell. IV. Th2 clones secrete a factor that inhibits cytokine production by Th1 clones," J. Exp. Med., 170(6):2081-2095.
George et al., (2003). "An analysis of protein domain linkers: their classification and role in protein folding," Protein Engineering, Design and Selection, 15:871-879.
Henikoff et al., (1992). "Amino acid substitution matrices from protein blocks," PNAS USA, 89:10915-10919.
Howard et al., (1989). "Intracerebral drug delivery in rats with lesion-induced memory deficits," J. Neurosurg., 71:105-112.
Hu et al. (2010) "Systemic delivery of an oncolytic adenovirus expressing soluble transforming growth factor-13 receptor I I-Fe fusion protein can inhibit breast cancer bone metastasis in a mouse model," Hum. Gene Ther., 21(11):1623-9.
Hu et al., (2010). "A modified hTERT promoter-directed oncolytic adenovirus replication with concurrent inhibition of TGFbeta signaling for breast cancer therapy." Cancer Gene Ther., 17(4):235-43.
International Search Report for PCT/US2017/053765 dated Feb. 21, 2018, 12 pages.
International Search Report for PCT/US2018/053197 dated Jan. 7, 2019, 10 pages.
Isaka et al., (1999). "Gene therapy by transforming growth factor-beta receptor-IgG Fc chimera suppressed extracellular matrix accumulation in experimental glomerulonephritis." Kidney Int., 55(2):465-75.
Joliot et al., (1991). "Antennapedia homeobox peptide regulates neural morphogenesis," Proc. Natl. Acad. Sci. USA, 88:1864-1868.
Karlin et al., (1990). "Methods for assessing the statistical significance of molecular sequence features by using general scoring schemes," PNAS, 87:2264-2268.
Kotenko et al., (1997). "Identification and Functional Characterization of a Second Chain of The Interleukin-10 Receptor Complex," The EMBO Journal, 16:5894-5903.
Linderholm et al., (2014). "Immunoglobulin Fc-Fusion Proteins Part 1: Their design and manufacture" Oct. 16, 2014. Retrieved online on Jan. 24, 2018 from <http://www.bioprocessintl.com/manufacturing/monoclonal-antibodies/immunoglobulinfc-fusion-proteins-part-I-design-manufacture/>, 11 pages.
Tatsis et al., (2004). "Adenoviruses as vaccine vectors," Mol Ther., 10(4):616-29.
Taylor (2009) "Review of the activation of TGF-beta in immunity," J. Leukoc. Biol., 85(1):29-33.
Written Opinion for PCT/US2017/053765 dated Feb. 21, 2018, 8 pages.
Written Opinion for PCT/US2018/053197 dated Jan. 7, 2019, 9 pages.
Wu et al., (1987). "Receptor-mediated in Vitro Gene Transformation by a Soluble DNA Carrier System," J. Biol. Chem., 262:4429-4432.
Zhang et al. (2015) "A novel immunocompetent murine model for replicating oncolytic adenoviral therapy," Cancer Gene Ther., 22(1):17-22.
Search Report received for Chinese Patent Application No. 201780073371.4 completed on Nov. 3, 2022, 8 pages.
Zheng et al., (2012). "A Novel Hybrid Adenotetroviral Vector with More extensive E3 deletion extends transgene expression in submandibular glands," Human Gene Therapy Methods, 23(3):169-81.

* cited by examiner

Human CH1 domains

```
IgA1  PKVFPLS......LCSTQPDGNV-......VIACLVQGf.....fPQEPLSVTWSESCGqv.....taRNFPPSQDASGDL.....YTTSSQLTLPA.....TQCLAGKSVTCHVKH......---YTNPSQDVT
IgA2  PKVFPLS......LDSTPQDGNV-......VVACLVQGf.....fPQEPLSVTWSESGQnv.....taRNFPPSQDASGDL.....YTTSSQLTLPA.....TQCPDGKSVTCHVKH......---YTNPSQDVT
IgD   PDVFPIis.....GCRHPKDNSPV......VLACLITGy.....HEtSVTVTWMGTQsq......PQRTFPEIQRRDSY.....IMTSSQLSTP-.....LQQWRQGEYKCVVQH......---TASKSKELF
IgE   PSVFPLtr.....cCKNIPSNATSV.....TLGCLATGy.....FRPVMVTWDIGSLn......GTTMTLPATTLTLsg..hYATISLLTVSG.....---AWAKQMFTCRVAHt....pSSTDWDNKTFS
IgG1  PSVFPLA......PSSKSTSGGTA......ALGCLVKDy.....FPEPVTVSWNSGALts.....gVHTFPAVLQSSGL.....YSLSSVVTVPS.....--SSLGTQTYICNVNH......KPSNTKVDKKVE
IgG2  PSVFPLA......PCSRSTSESTA......ALGCLVKDy.....FPEPVTVSWNSGALts.....gVHTFPAVLQSSGL.....YSLSSVVTVPS.....--SNFGTQTYTCNVDH......KPSNTKVDKTVE
IgG3  PSVFPLA......PCSRSTSGGTA......ALGCLVKDy.....FPEPVTVSWNSGALts.....gVHTFPAVLQSSGL.....YSLSSVVTVPS.....--SSLGTQTYTCNVNH......KPSNTKVDKRVE
IgG4  PSVFPLA......PCSRSTSESTA......ALGCLVKDy.....FPEPVTVSWNSGALts.....gVHTFPAVLQSSGL.....YSLSSVVTVPS.....--SSLGTKTYTCNVDH......KPSNTKVDKRVE
IgM   PTLFPLVs.....CENSPSDTSSV......AVGCLAQDf.....LPDSITLSWKYKNN......SDISSTRGFPSVLrg..gKYAATSQVLLPSk....dVMQGTDEHVVCKVQH......---PNGNKEKNVP
```

Human CH2 domains

```
IgA1  PRLSLHRp.....ALEDLLLGSEA......NLTCTLTGl.....rDASGVTFTWTPSSG..............KSAVQGPPERDLCg...cYSVSSVLPGCA.....EPWNHGKTFTCTAAY.....PESKTPLTATLS
IgA2  PRLSLHRp.....ALEDLLLGSEA......NLTCTLTGl.....rDASGATFTWTPSSG..............KSAVQGPPERDLCg...cYSVSSVLPGCA.....QPWNHGETFTCTAAH.....PELKTPLTANIT
IgD   PAVQDL-......-MLRDKA--......TFTCFVVGs.....DLKDAHLTWEVAGKvqt........ggvEEGLLERHSNGS-......QSQHSRLTLPR......SLMNAGTSVTCTINH......---PSLPPQRIMA
IgE   PTVKIL-......-QSSCDGGGHFpp..tiQLLCLVSGy....TPGTINITFWLEDGQvm......dvDLSTASTTQEGEL......ASTQSELTLSQ......KHWLSDRTYTCQVTYq.....GHTFEDSTKKCA
IgG1  PSVFLFPp.....KPKDTLMISRTP.....EVTCVVVDvs...hEDPEVKFNWYVDGVev........hnAKTKPREEQYNST......YRVVSVLTVLH......QDWLNGKEYKCKVSN......KALPAPIEKTIS
IgG2  PSVFLFPp.....KPKDTLMISRTP.....EVTCVVVDvs...hEDPEVQFNWYVDGVe.........VENAKTKPREEQFns.....tFRVVSVLTVVH......QDWLNGKEYKCKVSN......KGLPAPIEKTIS
IgG3  PSVFLFPp.....KPKDTLMISRTP.....EVTCVVVDvs...hEDPEVQFKWYVDGVev........hnAKTKPREEQYNST......FRVVSVLTVLH......QDWLNGKEYKCKVSN......KALPAPIEKTIS
IgG4  PSVFLFPp.....KPKDTLMISRTP.....EVTCVVVDvs...qEDPEVQFNWYVDGVe.........VENAKTKPREEQFns.....tYRVVSVLTVLH......QDWLNGKEYKCKVSN......KGLPSSIEKTIS
IgM   PKVSVFV......PPRDGFFGNPRk....sKLICQATGf...SERQIQVSWLREGKGvysg..vttdQVQAEFAKESGPTT....YKVTSTLTIKE......SDWLGQSMFTCRVDH.....---RGLTFQQNAS
```

FIGURE 2

HUMAN IL-10 RECEPTOR ALPHA FUSION PROTEINS

CROSS REFERENCE TO RELATED APPLICATIONS

This application is a § 371 National Stage of International (PCT) Patent Application No. PCT/US2018/053197, filed Sep. 27, 2018, which claims the benefit of, and priority to, U.S. provisional patent application No. 62/564,145, filed Sep. 27, 2017, the entire disclosures of each of which are hereby incorporated by reference herein for all purposes.

FIELD OF THE INVENTION

The field of the invention is molecular biology, specifically immunology and fusion proteins, e.g., cytokine receptor fusion proteins.

BACKGROUND

Cytokines are small, secreted cell signaling proteins that have a wide range of activities including regulation of cell growth and differentiation and modulation of immune function. Cytokines, cytokine receptors, and certain other immunomodulatory proteins have been used as therapeutics to treat a variety of medical conditions. However, the administration of such proteins, for example, by subcutaneous or vascular routes, can result in inappropriate cellular and extracellular localization thereby limiting therapeutic activity and/or increasing the risk of toxicity.

IL-10 is a homodimeric cytokine with immunoregulatory properties produced by cells including activated Th2 cells, B cells, keratinocytes, monocytes and macrophages (Moore et al. (1993) ANNU. REV. IMMUNOL. 11:165). IL-10 inhibits activation and effector functions of a variety of cells including T cells, monocytes and macrophages. In particular, IL-10 inhibits cytokine synthesis, including that of IL-1, IFN-γ, and TNF, by cells such as Th1 cells, natural killer cells, monocytes, and macrophages (Fiorentino et al. (1989) J. EXP. MED. 170:2081-2095; Fiorentino et al. (1991) J. IMMUNOL. 146:3444; Hsu et al. (1992) INT. IMMUNOL. 4:563; Hsu et al. (1992) INT. IMMUNOL. 4:563; D'Andrea et al. (1993) J. EXP. MED. 178:1041; de Waal Malefyt et al. (1991) J. EXP. MED. 174:915; Fiorentino et al. (1991) J. IMMUNOL. 147: 3815). Multiple pathogens, including intracellular pathogens, elicit IL-10 production to slow or stall the effective removal of the pathogen by the immune system (Moore et al. (1993) supra).

Despite the advances that have been made to date in treating IL-10 mediated disorders, there is a need for improved therapies for treating such disorders.

SUMMARY OF THE INVENTION

The invention is based, in part, upon the discovery of linker sequences that improve the function of fusion proteins, e.g., cytokine receptor fusion proteins, e.g., IL-10 receptor (IL-10R) fusion proteins, e.g., IL-10 receptor subunit alpha (IL-10RA) fusion proteins, e.g., IL-10 traps. The linker sequences may permit a ligand binding portion of a fusion protein (e.g., a cytokine receptor) to bind optimally to a ligand (e.g., a cytokine), provide temporal and spatial colocalization of two or more components of a fusion protein (e.g., two subunits of a dimeric cytokine), optimize expression from an expression vector (e.g., a viral vector), reduce immunogenicity, or provide a cleavage site to allow for release of a component of the fusion protein. For example, the linker sequences may provide sufficient flexibility to allow a ligand binding domain of a cytokine receptor to adopt a native conformation in the context of a fusion protein, and minimize the potential immunogenicity of the fusion protein for use as a therapeutic agent.

In one aspect, the invention provides an isolated fusion protein that comprises, for example, in an N- to C-terminal orientation: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; and an immunoglobulin (Ig) Fc domain. In certain embodiments, the linker comprises from about 5 to about 40 amino acid residues. In certain embodiments, the fusion protein comprises a portion of an IL-10 receptor, e.g., a human IL-10 receptor, e.g., IL-10RA.

In another aspect, the invention provides an isolated fusion protein that comprises, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues. In certain embodiments, the cytokine receptor is an IL-10 receptor, e.g., a human IL-10 receptor, e.g., IL-10RA.

In certain embodiments of any of the foregoing fusion proteins, the amino acid linker may comprise, e.g., from about 5 to about 15, from about 5 to about 20, from about 5 to about 30, from about 10 to about 15, from about 10 to about 20, from about 10 to about 30, from about to about 40, from about 15 to about 20, from about 15 to about 30, or from about 15 to about amino acid residues.

In certain embodiments of any of the foregoing fusion proteins, the amino acid linker sequence is derived from an endogenous human protein, e.g., IgG1, IgG2, IgG3, IgG4, IgA1, IgA2, IgD, IgE, IgM, albumin, or casein. In certain embodiments, the amino acid linker comprises a C-terminal portion of an immunoglobulin (Ig) CH1 domain, e.g., an IgG1, IgG2, IgG3, IgG4, IgA1, IgA2, IgD, IgE, or IgM CH1 domain. In certain embodiments, the amino acid linker comprises an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 53, SEQ ID NO: 54, and SEQ ID NO: 57. In certain embodiments, the amino acid linker comprises a C-terminal portion of an IgG1 CH1 domain, e.g., the amino acid linker comprises an amino acid sequence selected from SEQ ID NO: 1, SEQ ID NO: 53, SEQ ID NO: 54, and SEQ ID NO: 57, e.g., the amino acid sequence of SEQ ID NO: 57.

In certain embodiments of any of the foregoing fusion proteins, the amino acid linker comprises a sequence derived from a cytokine, signaling molecule, immunomodulatory protein or peptide, or a biologically active peptide.

In certain embodiments of any of the foregoing fusion proteins, the amino acid linker comprises a cleavage site, e.g., a proteolytic cleavage site, e.g., a proteolytic cleavage site that is cleaved by a protease present in the endoplasmic reticulum or golgi of a eukaryotic cell. In certain embodiments, the proteolytic cleavage site is a furin cleavage site, e.g., a furin cleavage site comprising the sequence $RX_1X_2R$ (SEQ ID NO: 50), wherein $X_1$ is any amino acid, and $X_2$ is Lys or Arg, e.g., a furin cleavage site comprising the sequence RAKR (SEQ ID NO: 51). In certain embodiments of any of the foregoing fusion proteins, the amino acid linker is proteolytically stable in a mammal or plant.

In certain embodiments of any of the foregoing fusion proteins, the soluble portion of an extracellular domain of a cytokine receptor is a soluble portion of an extracellular domain of the human IL-10R, e.g., IL-10RA. For example, in certain embodiments, the soluble portion of an extracellular domain of a cytokine receptor comprises the amino acid sequence of SEQ ID NO: 12 or amino acid residues 22-229 of SEQ ID NO: 12.

In certain embodiments of any of the foregoing fusion proteins, the fusion protein comprises one or more of IL-10, TGF-α, a TGFβ receptor, e.g., the TGFβ type II receptor (TβRII), CD80, CD19, CD20, IL-1, IL-2, IL-3, IL-4, IL-5, IL-6, IL-7, IL-8, IL-9, IL-12B/p40, IL-23A/p19, IL27A/p28, IL-27B/EBI3, IL-15, CD154, CD70, TNF-alpha, CD86, CD137, CD137L, BORIS/CTCFL, FGF, ICAM, IL-24, GM-CSF, MAGE, NY-ESO-1, angiostatin, endostatin, acetylcholine, interferon-gamma, DKK1/Wnt, p53, Ox40L, GM-CSF, an IL-15 receptor fusion protein, GITRL, CD40L, CD70, secreted flagellin, IL-12, thymidine kinase, an anti-PD-1 antibody heavy chain or light chain, an anti-PD-L1 antibody heavy chain or light chain, and an anti-CTLA-4 antibody heavy chain or light chain, or a functional fragment thereof.

In certain embodiments of any of the foregoing fusion proteins, the Ig hinge region is selected from an IgG1, IgG2, IgG3, IgG4, IgA1, IgA2, IgD, IgE, and IgM hinge region, and the Ig Fc domain, is selected from IgG1, IgG2, IgG3, IgG4, IgA1, IgA2, IgD, IgE, and IgM Fc domain. In certain embodiments, the Ig hinge region and Fc domain together comprise an amino acid sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21. In certain embodiments, the Ig Fc, Ig hinge region, and Ig CH1 domain are derived from a single immunoglobulin.

In certain embodiments of any of the foregoing fusion proteins, the fusion protein comprises an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 55, SEQ ID NO: 56, and SEQ ID NO: 58. In certain embodiments, the fusion protein comprises an amino acid sequence selected from SEQ ID NO: 22, SEQ ID NO: 55, SEQ ID NO: 56, and SEQ ID NO: 58. In certain embodiments, the fusion protein comprises the amino acid sequence of SEQ ID NO: 58.

In certain embodiments of any of the foregoing fusion proteins, the fusion protein comprises an amino acid sequence having greater than 80%, 85%, 90%, 95%, 96%, 97%, 98% or 99% sequence identity to a sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 55, SEQ ID NO: 56, and SEQ ID NO: 58.

In another aspect, the invention provides a dimeric cytokine binding protein comprising two of any of the foregoing fusion proteins covalently linked together, wherein each fusion protein comprises an extracellular domain of a cytokine receptor, and wherein the two extracellular domains together define a binding site for a cytokine.

In another aspect, the invention provides a nucleic acid comprising a nucleotide sequence that encodes for any of the foregoing fusion proteins.

In another aspect, the invention provides an expression vector comprising any of the foregoing nucleic acids.

In another aspect, the invention provides a host cell comprising any of the foregoing expression vectors. In another aspect, the invention provides a method of producing a fusion protein comprising growing a host cell under conditions to express the fusion protein and purifying the fusion protein. In another aspect, the invention provides a method of expressing a fusion protein in a target cell comprising exposing the cell to an effective amount of any of the foregoing expression vectors. In certain embodiments, the fusion protein is cleaved posttranslationally into two polypeptide chains.

In another aspect, any of foregoing fusion proteins or expression vectors can be used, e.g., to reduce cytokine activity in a subject, thereby treating various medical indications that are mediated by a cytokine, for example, IL-10. In another aspect, any of the foregoing fusion proteins or expression vectors can be used to inhibit proliferation of tumor cells in vitro and/or in vivo, inhibit tumor growth in a subject in need thereof, or treat cancer in a subject in need thereof. The subject may be, e.g., an animal, e.g., a mammal, e.g., a human, e.g., a pediatric human. For example, when administered to a human subject with cancer, the fusion proteins or expression vectors inhibit or reduce tumor growth, or, reduce the tumor load, in the subject.

In certain embodiments, the cancer may be selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, liver cancer, hepatocellular carcinoma, cholangiocarcinoma, brain and central nervous system cancer, thyroid cancer, parathyroid cancer (e.g., parathyroid carcinoma), endometrial cancer, neuroendocrine cancer, lymphoma (e.g., Hodgkin and non-Hodgkin), leukemia, merkel cell carcinoma, gastrointestinal stromal tumors, multiple myeloma, uterine cancer, a sarcoma, kidney cancer, ocular cancer, pancreatic cancer, and a germ cell cancer (e.g., ovarian germ cell cancer). In certain embodiments, the cancer may be selected from leukemia, breast cancer, lung cancer, pancreatic cancer, endometrial cancer, ovarian cancer, prostate cancer, cervical cancer, brain cancer, skin cancer, colorectal cancer, gastric cancer, head and neck cancer, and leukemia.

In certain embodiments, the fusion protein or expression vector is administered in combination with one or more therapies selected from surgery, radiation, chemotherapy, immunotherapy, hormone therapy, and virotherapy. In certain embodiments, the fusion protein or expression vector is administered in combination with a lymphocyte, e.g., a T-cell, e.g., a CAR T-cell.

Any of the foregoing fusion proteins or expression vectors can also be used to treat an inflammatory condition or infection in a subject in need thereof.

These and other aspects and advantages of the invention are illustrated by the following figures, detailed description and claims.

DESCRIPTION OF THE DRAWINGS

The invention can be more completely understood with reference to the following drawings.

FIG. 2 depicts a sequence alignment of the amino acid sequences of the human IgG1, IgG2, IgG3, IgG4, IgA1, IgA2, IgD, IgE, and IgM CH1 domains (top) and CH2 domains (bottom).

DETAILED DESCRIPTION

The invention provides a recombinant fusion protein for use in the treatment of a variety of medical conditions, for example, in inhibiting proliferation of a tumor cell, inhibiting tumor growth, treating cancer, treating an inflammatory condition, or treating an infection, in a subject. Exemplary fusion proteins comprise: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; or an immunoglobulin (Ig) Fc domain. It is contemplated that the first and second portions can be portions of the same protein or portions of different proteins, and, even if the same protein, the first and second portions can be different portions of the same protein. In certain embodiments, the linker comprises from about 5 to about 40 amino acid residues. Exemplary fusion proteins of the invention include cytokine traps.

A cytokine trap, e.g. an IL-10 trap, is a molecule containing a soluble portion of the extracellular domain of a cytokine receptor, e.g., an IL-10 receptor (IL-10R), e.g., an IL-10 receptor alpha subunit (IL-10RA) designed to bind or otherwise sequester a target cytokine. In a cytokine trap, the extracellular domain of a cytokine receptor may be fused to an immunoglobulin (Ig) hinge region and immunoglobulin (Ig) Fc domain which can allow, e.g., for increased stability, Fc effector functions and/or multimerization, e.g., dimerization. Dimerization afforded by fusion to an Ig hinge region and Ig Fc domain is particularly advantageous for cytokine receptors that exist as dimeric receptor complexes on the cellular surface, such as, e.g., TβRII.

Figure 1A:
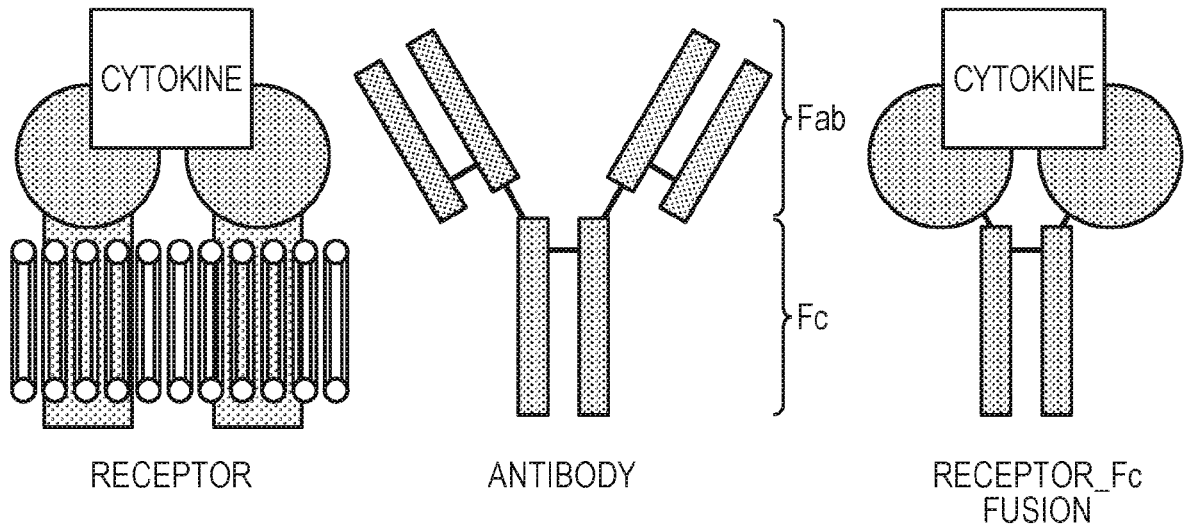
FIG. 1A depicts a schematic of a dimeric cytokine receptor on the cell surface (left), an antibody (middle), and a receptor-Fc fusion that optimally binds a target cytokine (right).

Conventional cytokine traps, e.g., IL-10 traps, comprise two polypeptide chains, each polypeptide chain comprising a soluble portion of an extracellular domain of a cytokine receptor fused to an Ig hinge region and an Ig Fc domain. The soluble portion of the extracellular domain of the cytokine receptor typically is fused directly to the Ig hinge region, without any intervening sequence. The two polypeptide chains are covalently linked by disulfide bonds between cysteine residues in each of the Ig hinge regions. Each polypeptide chain provides a soluble portion of an extracellular domain of a cytokine receptor, e.g., IL-10R, e.g., IL-10RA, and the two soluble portions of an extracellular domain of a cytokine receptor together define a binding site for a cytokine. A schematic representation of a dimeric cytokine receptor, an immunoglobulin (antibody) molecule, and a dimeric protein comprising two covalently linked fusion proteins each comprising a soluble portion of an extracellular domain of a cytokine receptor fused to an Ig hinge region and an Ig Fc domain is depicted in FIG. 1A.

The invention is based, in part, upon the discovery that conventional cytokine traps comprising a fusion protein of a soluble portion of an extracellular domain of a cytokine receptor to an Ig hinge region and Ig Fc domain, e.g., IL-10 traps, do not optimally bind their target cytokine. For example, a conventional IL-10 trap does not provide sufficient flexibility between the two IL-10 ligand binding domains to allow the two IL-10 ligand binding domains to come together in an optimal configuration to define an IL-10 binding site.

Figure 1B:
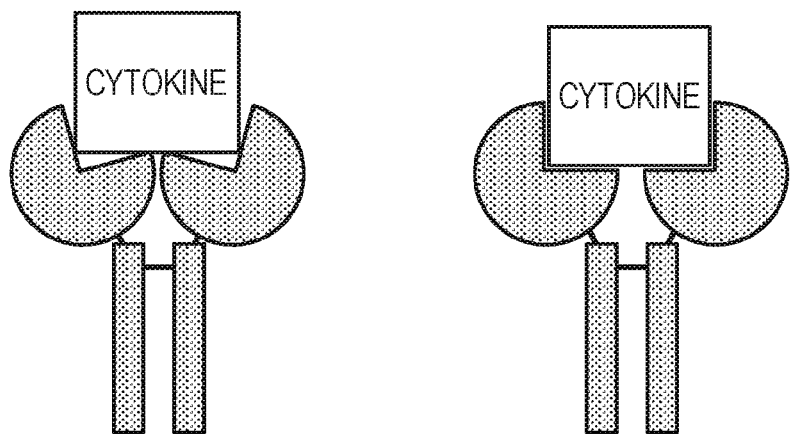
FIG. 1B depicts a receptor-Fc fusion, e.g., a cytokine trap, that is sterically constrained from optimal binding to a target cytokine (left), or that adopts an optimal binding configuration (right).
Figure 3:
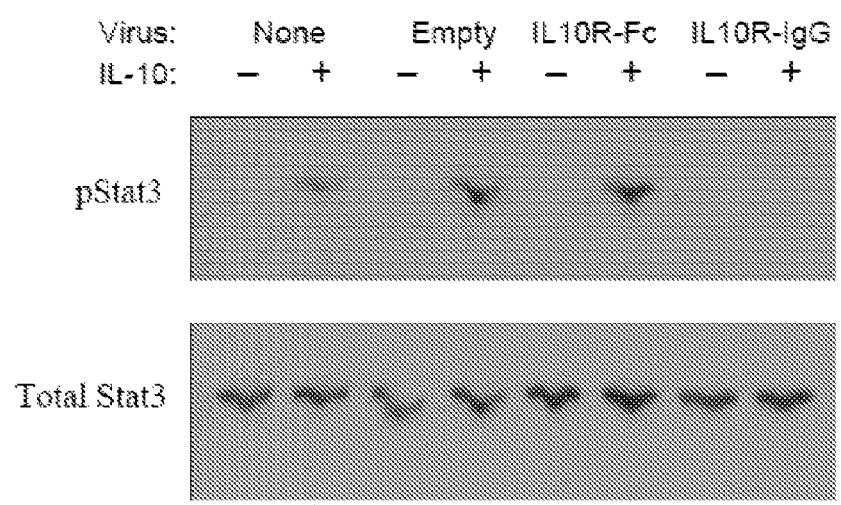
FIG. 3 depicts a Western blot for phosphorylated Stat3 following treatment of reporter cells with IL-10 and/or the IL-10RA fusion proteins IL-10R-IgG and IL-10R-Fc as indicated. Total Stat3 was used as a loading control. IL-10 activity was markedly reduced by IL-10R-IgG compared to IL-10R-Fc.

Thus, in one aspect, the invention provides an isolated fusion protein that comprises, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues. The linker sequence allows, e.g., the binding domain in the extracellular domain of the cytokine receptor to bind optimally to its target cytokine. This is especially important when the cytokine binding protein is a dimer that comprises two of the foregoing fusion proteins that together define a binding site to bind the target cytokine. Without the linker, the two binding domains may be sterically constrained from forming the optimal binding site (FIG. 1B). Various features and aspects of the invention are discussed in more detail below.

I. Fusion Proteins

Exemplary fusion proteins may comprise: a first portion of an extracellular domain, transmembrane domain, or intracellular domain of a cytokine, cytokine receptor, or immunomodulatory protein; an amino acid linker; and at least one of, a second portion of an extracellular domain, transmembrane domain, or intracellular domain of a cytokine, cytokine receptor, or immunomodulatory protein; an immunoglobulin (Ig) hinge region; and an immunoglobulin (Ig) Fc domain. For example, a disclosed fusion protein may comprise, in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues.

Exemplary cytokines include IL-1α, IL-1β, IL-18. IL-2, IL-4, IL-7, IL-9, IL-13, IL-15, IL-3, IL-5, GM-CSF, IL-6, IL-11, G-CSF, IL-12, LIF, OSM, IL-10, IL-20, IL-14, IL-16, IL-17, IFN-α, IFN-β, IFN-γ, CD154, LT-β, TNF-α, TNF-β, 4-1BBL APRIL, CD70, CD153, CD178, GITRL, LIGHT, OX40L, TALL-1, TRAIL, TWEAK, TRANCE, TGF-β1, TGF-β2, TGF-β3, Epo, Tpo, Flt-3L, SCF, M-CSF, and MSP.

As used herein, an "immunomodulatory" protein refers to a protein that modulates the function of the immune system of a subject Immunomodulatory proteins may, for example, modulate the function of, e.g., B-cells, T cells and/or the production of antibodies. Exemplary immunomodulatory proteins include checkpoint inhibitors. Exemplary immunomodulatory proteins may include, e.g., CTLA-4, CD70, IL-2, CD40L, OX40L, IL-12, IL-7, PD-1, or PD-L1, or any protein that modulates the activity thereof. Further exemplary immunomodulatory proteins may include an anti PD-1 antibody, or anti-PD-L1 antibody.

As used herein, a "soluble portion of an extracellular domain of a cytokine receptor" refers to any extracellular domain of a cytokine receptor or fragment of an extracellular domain of a cytokine receptor that is capable of binding to a target cytokine. It is understood that the soluble portion of an extracellular domain of a cytokine receptor also contemplates portions of the extracellular domain that comprise a binding domain that, either alone or in combination with a second binding domain (e.g., in the case of dimeric fusion proteins) is capable of binding to a target cytokine.

Exemplary cytokine receptors include type I cytokine receptors (e.g., GM-CSF receptors, G-CSF receptors, type I IL receptors, Epo receptors, LIF receptors, CNTF receptors, or TPO receptors), type II cytokine receptors (e.g., IL-10 receptors, IFN-alpha receptors (e.g., IFNAR1 or IFNAR2), IFN-beta receptors, IFN-gamma receptors (e.g., IFNGR1 or IFNGR2), chemokine receptors (e.g., CC chemokine receptors, CXC chemokine receptors, CX3C chemokine receptors, or XC chemokine receptors), tumor necrosis factor superfamily receptors (TNFRs; e.g., TNFRSF5/CD40, TNFRSF8/CD30, TNFRSF7/CD27, TNFRSF1A/TNFR1/CD120a, or TNFRSF1B/TNFR2/CD120b), TGFβ superfamily receptors (e.g., TGFβ type I receptor or TGFβ type II receptor), or immunoglobulin (Ig) superfamily receptors (e.g., interleukin-1 receptors, CSF-1R, PDGFR (e.g., PDGFRA or PDGFRB), or SCFR). Preferred cytokine receptors include dimeric cytokine receptors, e.g., TGFβ superfamily receptors, e.g., the human TGFβ type II receptor (TβRII). In certain embodiments, the soluble portion of an extracellular domain of a cytokine receptor is a soluble portion of an extracellular domain of the human IL-10R, e.g., human IL-10RA, e.g., comprising the amino acid sequence of SEQ ID NO: 12, or an amino acid sequence having greater than 85%, 90%, 95%, 96%, 97%, 98% or 99% sequence identity to SEQ ID NO: 12, and/or a fragment thereof that comprises a binding domain that binds to IL-10.

The soluble portion of the extracellular domain of a cytokine receptor retains its ability to bind its native ligand. In certain embodiments, the soluble portion of the extracellular domain retains at least 50%, 60%, 70%, 80%, 90%, or 95% of the binding activity to its native ligand when compared to the full length cytokine receptor.

In certain embodiments, the fusion protein can comprise, e.g., one or more of TβRII, TGF-α, CD80, CD19, CD20, IL-1, IL-2, IL-3, IL-4, IL-5, IL-6, IL-7, IL-8, IL-9, IL-12B/p40, IL-23A/p19, IL-27A/p28, IL-27B/EBI3, IL-15, CD154, CD70, TNF-alpha, CD86, CD137, CD137L, BORIS/CTCFL, FGF, ICAM, IL-24, GM-CSF, MAGE, NY-ESO-1, angiostatin, endostatin, acetylcholine, interferon-gamma, DKK1/Wnt, p53, Ox40L, GM-CSF, an IL-15 receptor fusion protein, GITRL, CD40L, CD70, secreted flagellin, IL-12, thymidine kinase, an anti-PD-1 antibody heavy chain or light chain, an anti-PD-L1 antibody heavy chain or light chain, and an anti-CTLA-4 antibody heavy chain or light chain, or a functional fragment thereof.

As used herein, the term "immunoglobulin (Ig) hinge region" refers to the amino acid sequence that typically connects CH1 and CH2 domains of an immunoglobulin heavy chain constant region. An Ig hinge region may include, e.g., one or more cysteine residues capable of forming disulfide bonds with cysteine residues in another protein chain. As used herein, the term "immunoglobulin (Ig) Fc domain" refers to a fragment of an immunoglobulin heavy chain constant region that is capable of binding to an Fc receptor. An Ig Fc domain may include, e.g., an immunoglobulin (Ig) CH2 and CH3 domain. Boundaries between Ig CH1, CH2, and CH3 domains are well known in the art, and can be found, e.g., in the PROSITE database (available on the world wide web at prosite.expasy.org). For clarity, alignments of the amino acid sequences of the human IgG1, IgG2, IgG3, IgG4, IgA1, IgA2, IgD, IgE, and IgM CH1 and CH2 domains are provided in FIG. 2.

In certain embodiments, the Ig hinge region is selected from an IgG1, IgG2, IgG3, IgG4, IgA1, IgA2, IgD, IgE, and IgM hinge region, and the Ig Fc domain, is selected from an IgG1, IgG2, IgG3, IgG4, IgA1, IgA2, IgD, IgE, and IgM Fc domain. In certain embodiments, the Ig hinge region and Fc domain together comprise an amino acid sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21. In certain embodiments, the Ig hinge region and Fc domain together comprise an amino acid sequence having greater than 85%, 90%, 95%, 96%, 97%, 98% or 99% identity with a sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

The amino acid linker may permit a ligand binding portion of a fusion protein (e.g., a cytokine receptor) to bind optimally to a ligand (e.g., a cytokine), provide temporal and spatial co-localization of two or more components of a fusion protein (e.g., two subunits of a dimeric cytokine), optimize expression from an expression vector (e.g., a viral vector), reduce immunogenicity, or provide a cleavage site to allow for release of a component of the fusion protein.

The amino acid linker may comprise, e.g., from about 5 to about 15, from about 5 to about 20, from about 5 to about 25, from about 5 to about 30, from about 5 to about 35, from about 5 to about 40, from about 10 to about 15, from about 10 to about 20, from about 10 to about 25, from about 10 to about 30, from about 10 to about 35, from about 10 to about 40, from about 15 to about 20, from about 15 to about 25, from about 15 to about 30, from about 15 to about 35, or from about 15 to about 40 amino acid residues. The amino acids in the linker can be naturally occurring amino acids or modified amino acids.

In certain embodiments, the amino acid linker sequence is derived from an endogenous human protein, e.g., IgG1, IgG2, IgG3, IgG4, IgA1, IgA2, IgD, IgE, IgM, albumin, or casein. In certain embodiments, the amino acid linker comprises a C-terminal portion, for example, from about 5 to about 40 amino acids, of an immunoglobulin (Ig) CH1 domain, e.g., an IgG1, IgG2, IgG3, IgG4, IgA1, IgA2, IgD, IgE, or IgM CH1 domain. In certain embodiments, the amino acid linker comprises an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 53, SEQ ID NO: 54, SEQ ID NO: 57, SEQ ID NO: 59, SEQ ID NO: 60, SEQ ID NO: 61, SEQ ID NO: 62, SEQ ID NO: 63, and SEQ ID NO: 64. In certain embodiments, the amino acid linker comprises a sequence having greater than 85%, 90%, 95%, 96%, 97%, 98% or 99% sequence identity to an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 53, SEQ ID NO: 54, SEQ ID NO: 57, SEQ ID NO: 59, SEQ ID NO: 60, SEQ ID NO: 61, SEQ ID NO: 62, SEQ ID NO: 63, and SEQ ID NO: 64.

A protein or polypeptide is "derived from" a reference protein or polypeptide if it comprises an amino acid sequence that is substantially similar to all or a corresponding portion of the wild-type amino acid sequence of the reference protein or polypeptide. In certain embodiments, a protein or polypeptide that is derived from a wild-type protein or polypeptide may have one or more amino acid substitutions relative to the wild-type protein or polypeptide. For example, it is contemplated that a protein or polypeptide that is derived from a wild-type protein or polypeptide may have greater than 70%, 75%, 80%, 85%, 90%, 95%, 96%, 97%, 98% or 99% sequence identity to the wild-type protein or polypeptide. Further, it is contemplated that a protein or polypeptide that is derived from a wild-type protein or polypeptide may contain on more conservative substitutions relative to the wild-type protein or polypeptide. As used herein, the term "conservative substitution" refers to a substitution with a structurally similar amino acid. For example, conservative substitutions may include those within the following groups: Ser and Cys; Leu, Ile, and Val; Glu and Asp; Lys and Arg; Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix).

In certain embodiments, the amino acid linker sequence is derived from a cytokine, signaling molecule, immunomodulatory protein or peptide, or a biologically active peptide.

Further contemplated linker sequences include glycine- and serine-rich linkers, e.g., $(G_4S)_3$ (SEQ ID NO: 49). Additional exemplary linker sequences are disclosed, e.g., in George et al. (2003) PROTEIN ENGINEERING 15:871-879 and U.S. Pat. Nos. 5,482,858 and 5,525,491.

In certain embodiments, the amino acid linker may comprise a cleavage site, e.g., a proteolytic or a non-proteolytic cleavage site. In certain embodiments, the proteolytic cleavage site is cleaved by a protease present in a specific tissue, organelle or intracellular compartment. In certain embodiments, the linker comprises a proteolytic cleavage site and two cysteine residues that result in a disulfide linkage following proteolytic cleavage. In certain embodiments, the proteolytic cleavage site is cleaved by a protease selected from a matrix metalloproteinase (MMP), furin, PC1, PC2, PC3, cathepsin B, proteinase 3, and caspase 3. In certain embodiments, the cleavage site is a proteolytic cleavage site that is cleaved by a protease that is present in the endoplasmic reticulum or golgi of a eukaryotic cell. In certain embodiments, the proteolytic cleavage site is a furin cleavage site. Furin is a protease that is ubiquitously expressed and is localized to the golgi, where it recognizes the consensus sequence $RX_1X_2R$ (SEQ ID NO: 50), wherein $X_1$ is any amino acid, and $X_2$ is Lys or Arg, and cleaves after the final Arg. Furin plays a biological role in cleaving propeptides of proteins that are trafficked through the golgi. Accordingly, in certain embodiments the proteolytic cleavage site is a furin cleavage site comprising the sequence $RX_1X_2R$ (SEQ ID NO: 50), wherein $X_1$ is any amino acid, and $X_2$ is Lys or Arg, e.g., a furin cleavage site comprising the sequence RAKR (SEQ ID NO: 51).

In certain embodiments, the Ig Fc, Ig hinge region, and Ig CH1 domain are derived from a single immunoglobulin.

In certain embodiments, the fusion protein comprises an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 55, SEQ ID NO: 56, and SEQ ID NO: 58. In certain embodiments, a disclosed fusion protein comprises an amino acid sequence having greater than 85%, 90%, 95%, 96%, 97%, 98% or 99% sequence identity to a sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 55, SEQ ID NO: 56, and SEQ ID NO: 58.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36, 290-300; Altschul et al., (1997) NUCLEIC ACIDS RES. 25:3389-3402, incorporated by reference) are tailored for sequence similarity searching. For a discussion of basic issues in searching sequence databases see Altschul et al., (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; —W, wordsize [Integer]: default=11 for nucleotides/28 for megablast/3 for proteins; −y, Dropoff (X) for blast extensions in bits: default=20 for blastn/7 for others; —X, X dropoff value for gapped alignment (in bits): default=for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In one aspect the invention provides a cytokine binding protein comprising two fusion proteins, wherein each fusion protein comprises in an N- to C-terminal orientation: a soluble portion of an extracellular domain of a cytokine receptor; an amino acid linker; an immunoglobulin (Ig) hinge region; and an immunoglobulin (Ig) Fc domain; wherein the linker comprises from about 5 to about 40 amino acid residues, wherein the two fusion proteins are covalently linked together, and wherein the two extracellular domains together define a binding site for a cytokine.

The cytokine binding protein may comprise two of the foregoing fusion proteins covalently linked together, wherein each fusion protein comprises an extracellular domain of a cytokine receptor, and wherein the two extracellular domains together define a binding site for a cytokine. The fusion proteins may be covalently linked, e.g., by disulfide bonds between cysteine residues in the Ig hinge region of each fusion protein. In certain embodiments, the fusion proteins, either monomeric or multimeric (e.g., dimeric) retain at least 50%, 60%, 70%, 80%, 90%, or 95% of the binding activity of the target ligand when compared to the native, full length cytokine receptor.

In certain embodiments, a cytokine binding protein of the invention binds a cytokine with a $K_D$ of 200 nM, 100 nM, 20 nM, 15 nM, 10 nM, 9 nM, 8 nM, 7 nM, 6 nM, 5 nM, 4 nM, 3 nM, 2 nM, 1 nM, 50 pM, 25 pM or lower. In certain embodiments, a cytokine binding protein of the invention binds a cytokine with a $K_D$ of from 200 nM to 100 nM, from 200 nM to 20 nM, from 200 nM to 10 nM, from 200 nM to 5 nM, from 200 nM to 1 nM, from 200 nM to 50 pM, from 200 nM to 25 pM, from 100 nM to 20 nM, from 100 nM to 10 nM, from 100 nM to 5 nM, from 100 nM to 1 nM, from 100 nM to 50 pM, from 100 nM to 25 pM, from 20 nM to 10 nM, from nM to 5 nM, from 20 nM to 1 nM, from 20 nM from 100 nM to 50 pM, from 100 nM to 25 pM, 20 nM to 10 nM, from 20 nM to 5 nM, from 20 nM to 1 nM, from 20 nM to 50 pM, from 20 nM to 25 pM, from 10 nM to 5 nM, from 10 nM to 1 nM, from 10 nM to 50 pM, from 10 nM to 25 pM, from 5 nM to 1 nM, from 5 nM to 50 pM, from 5 nM to 25 pM, from 1 nM to 50 pM, from 1 nM to 25 pM, or from 50 pM to 25 pM. $K_D$ values may be determined by methods well known in the art, including surface plasmon resonance or bio-layer interferometry methods.

Exemplary fusion proteins of the invention include proteins comprising an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 55, SEQ ID NO: 56, and SEQ ID NO: 58. For clarity, the sequences of the individual elements of these proteins, and the proteins from which the sequences of the individual elements were derived, including the soluble portion of an extracellular domain of a cytokine receptor, the amino acid linker, the Ig hinge region, and the Ig Fc domain, are set forth in TABLE 1.

TABLE 1

| Protein | Receptor Source Receptor SEQ ID | Linker Source Linker SEQ ID | Ig Hinge/Ig Fc Source Ig Hinge/Ig Fc SEQ ID |
|---|---|---|---|
| SEQ ID NO: 22 | IL-10RA SEQ ID NO: 12 | IgG1 CH1 domain SEQ ID NO: 1 | IgG1 SEQ ID NO: 13 |
| SEQ ID NO: 55 | IL-10RA SEQ ID NO: 12 | IgG1 CH1 domain SEQ ID NO: 53 | IgG1 SEQ ID NO: 13 |
| SEQ ID NO: 56 | IL-10RA SEQ ID NO: 12 | IgG1 CH1 domain SEQ ID NO: 54 | IgG1 SEQ ID NO: 13 |
| SEQ ID NO: 58 | IL-10RA SEQ ID NO: 12 | IgG1 CH1 domain SEQ ID NO: 57 | IgG1 SEQ ID NO: 13 |
| SEQ ID NO: 23 | IL-10RA SEQ ID NO: 12 | IgG2 CH1 domain SEQ ID NO: 2 | IgG2 SEQ ID NO: 14 |
| SEQ ID NO: 24 | IL-10RA SEQ ID NO: 12 | IgG3 CH1 domain SEQ ID NO: 3 | IgG3 SEQ ID NO: 15 |
| SEQ ID NO: 25 | IL-10RA SEQ ID NO: 12 | IgG4 CH1 domain SEQ ID NO: 4 | IgG4 SEQ ID NO: 16 |
| SEQ ID NO: 26 | IL-10RA SEQ ID NO: 12 | IgA1 CH1 domain SEQ ID NO: 5 | IgA1 SEQ ID NO: 17 |
| SEQ ID NO: 27 | IL-10RA SEQ ID NO: 12 | IgA2 CH1 domain SEQ ID NO: 6 | IgA2 SEQ ID NO: 18 |
| SEQ ID NO: 28 | IL-10RA SEQ ID NO: 12 | IgD CH1 domain SEQ ID NO: 7 | IgD SEQ ID NO: 19 |
| SEQ ID NO: 29 | IL-10RA SEQ ID NO: 12 | IgE CH1 domain SEQ ID NO: 8 | IgE SEQ ID NO: 20 |
| SEQ ID NO: 30 | IL-10RA SEQ ID NO: 12 | IgM CH1 domain SEQ ID NO: 9 | IgM SEQ ID NO: 21 |
| SEQ ID NO: 31 | IL-10RA SEQ ID NO: 12 | Albumin SEQ ID NO: 10 | IgG1 SEQ ID NO: 13 |
| SEQ ID NO: 32 | IL-10RA SEQ ID NO: 12 | Casein SEQ ID NO: 11 | IgG1 SEQ ID NO: 13 |
| SEQ ID NO: 33 | ImIL-10RA SEQ ID NO: 34 | mIgG1 CH1 domain SEQ ID NO: 35 | mIgG1 SEQ ID NO: 36 | to 50 pM, from 20 nM to 25 pM, from 10 nM to 5 nM, from 10 nM to 1 nM, from 10 nM to 50 pM, from 10 nM to 25 pM, from 5 nM to 1 nM, from 5 nM to 50 pM, from 5 nM to 25 pM, from 1 nM to 50 pM, from 1 nM to 25 pM, or from 50 pM to 25 pM. In certain embodiments, a cytokine binding protein of the invention binds IL-10 with a $K_D$ of 200 nM, 100 nM, 20 nM, 15 nM, 10 nM, 9 nM, 8 nM, 7 nM, 6 nM, 5 nM, 4 nM, 3 nM, 2 nM, 1 nM, 50 pM, 25 pM or lower. In certain embodiments, a cytokine binding protein of the invention binds IL-10 with a $K_D$ of from 200 nM to 100 nM, from 200 nM to 20 nM, from 200 nM to 10 nM, from 200 nM to 5 nM, from 200 nM to 1 nM, from 200 nM to 50 pM, from 200 nM to 25 pM, from 100 nM to 20 nM, from 100 nM to 10 nM, from 100 nM to 5 nM, from 100 nM to 1 nM,

TABLE 2

| Protein Sequence | Nucleic Acid Sequence |
|---|---|
| SEQ ID NO: 22 | SEQ ID NO: 37 |
| SEQ ID NO: 23 | SEQ ID NO: 38 |
| SEQ ID NO: 24 | SEQ ID NO: 39 |
| SEQ ID NO: 25 | SEQ ID NO: 40 |
| SEQ ID NO: 26 | SEQ ID NO: 41 |
| SEQ ID NO: 27 | SEQ ID NO: 42 |
| SEQ ID NO: 28 | SEQ ID NO: 43 |
| SEQ ID NO: 29 | SEQ ID NO: 44 |
| SEQ ID NO: 30 | SEQ ID NO: 45 |
| SEQ ID NO: 31 | SEQ ID NO: 46 |
| SEQ ID NO: 32 | SEQ ID NO: 47 |

II. Fusion Protein Production

Methods for producing fusion proteins of the invention are known in the art. For example, DNA molecules encoding a disclosed fusion protein can be chemically synthesized using the sequence information provided herein. Synthetic DNA molecules can be ligated to other appropriate nucleotide sequences, including, e.g., expression control sequences, to produce conventional gene expression constructs encoding the desired fusion protein. Production of defined gene constructs is within routine skill in the art. Exemplary nucleic acid sequences SEQ ID NOs: 37-47, which encode the fusion proteins of SEQ ID NOs: 22-32, can be found in TABLE 2.

Nucleic acids encoding desired fusion proteins can be incorporated (ligated) into expression vectors, which can be introduced into host cells through conventional transfection or transformation techniques. Exemplary host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the desired fusion protein.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. The gene construct can be introduced into eukaryotic host cells using conventional techniques.

A polypeptide comprising a disclosed fusion protein can be produced by growing (culturing) a host cell transfected with an expression vector encoding such protein, under conditions that permit expression of the polypeptide. Following expression, the polypeptide can be harvested and purified or isolated using techniques known in the art, e.g., affinity tags such as Protein A, Protein G, glutathione-S-transferase (GST) and histidine tags.

III. Expression Vectors

The fusion proteins of interest may be expressed in a cell of interest by incorporating a gene encoding a fusion protein of interest into an appropriate expression vector. As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide of interest.

In certain embodiments, a disclosed expression vector is a viral vector. The terms "viral vector" and "virus" are used interchangeably herein to refer to any of the obligate intracellular parasites having no protein-synthesizing or energy-generating mechanism. The viral genome may be RNA or DNA. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. The viruses may be modified by recombinant DNA techniques to include expression of exogenous transgenes and may be engineered to be replication deficient, conditionally replicating, or replication competent. Chimeric viral vectors which exploit advantageous elements of each of the parent vector properties (See, e.g., Feng et al. (1997) NATURE BIOTECHNOLOGY 15:866-870) may also be useful in the practice of the present invention. Although it is generally favored to employ a virus from the species to be treated, in some instances it may be advantageous to use vectors derived from different species that possess favorable pathogenic features. For example, equine herpes virus vectors for human gene therapy are described in PCT Publication No. WO 98/27216. The vectors are described as useful for the treatment of humans as the equine virus is not pathogenic to humans. Similarly, ovine adeno-viral vectors may be used in human gene therapy as they are claimed to avoid the antibodies against the human adenoviral vectors. Such vectors are described in PCT Publication No. WO 97/06826.

In certain embodiments, the viral vector is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are vectors derived from human adenovirus types 2 and 5. Unless stated otherwise, all adenovirus type 5 nucleotide numbers are relative to the NCBI reference sequence AC_000008.1, which is depicted herein in SEQ ID NO: 52.

The adenovirus replication cycle has two phases: an early phase, during which 4 transcription units (E1, E2, E3, and E4) are expressed, and a late phase which occurs after the onset of viral DNA synthesis, and during which late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

IV. Fusion Protein Modifications

When used as a therapeutic, a fusion protein may be optimized (e.g., affinity-matured) to improve biochemical characteristics including affinity and/or specificity, improve biophysical properties including aggregation, stability, precipitation and/or non-specific interactions, and/or to reduce immunogenicity. Affinity-maturation procedures are within ordinary skill in the art. For example, diversity can be introduced into a disclosed fusion protein by DNA shuffling, chain shuffling, CDR shuffling, random mutagenesis and/or site-specific mutagenesis.

Generally, an optimized fusion protein has at least the same, or substantially the same (e.g., at least 85%, 90%, 95%, 96%, 97%, 98%, or 99%) affinity for a ligand as the non-optimized (or parental) fusion protein from which it was derived. Preferably, an optimized fusion protein has a higher affinity for a ligand when compared to a parental fusion protein.

Fusion proteins (e.g., parental and optimized variants) can be engineered to contain certain constant (i.e., Fc) regions with a specified effector function (e.g., antibody-dependent cellular cytotoxicity (ADCC)). Human constant regions are known in the art.

Furthermore, if the fusion protein is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

V. Methods of Treatment

The foregoing fusion proteins or expression vectors can be used to treat various medical indications. In certain embodiments, the foregoing fusion proteins or expression vectors can be used to treat medical indications that are mediated by a cytokine, for example IL-10. For example, the fusion proteins and expression vectors can be used to treat various cancers or inflammatory diseases.

As used herein, "treat," "treating" and "treatment" mean the treatment of a disease in a subject, e.g., in a mammal, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

In certain embodiments, the fusion proteins and expression vectors disclosed herein can be used to treat various cancers. The cancer cells are exposed to a therapeutically effective amount of the fusion protein or expression vector so as to inhibit or reduce proliferation of the cancer cells. In certain embodiments, administering a therapeutically effective amount of a fusion protein or expression vector to cancer cells reduces IL-10 activity in the cells by at least 30%, at least 40%, at least 50%, at least 60%, at least 70%, at least 80%, at least 90%, or at least 95%. IL-10 activity may be assayed by Western blot as described in Example 2. In some embodiments, a disclosed fusion protein or expression vector can be used to inhibit tumor growth in a subject (e.g., a human patient, also referred to as a human subject), which can be accomplished by administering an effective amount of the fusion protein or expression vector to the subject. In certain embodiments, administering an effective amount of a fusion protein or expression vector to a subject reduces tumor load in that subject by at least 30%, at least 40%, at least 50%, at least 60%, at least 70%, at least 80%, or at least 90%.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, liver cancer, hepatocellular carcinoma, cholangiocarcinoma, brain and central nervous system cancer, thyroid cancer, parathyroid cancer (e.g., parathyroid carcinoma), endometrial cancer, neuroendocrine cancer, lymphoma (e.g., Hodgkin and non-Hodgkin), leukemia, merkel cell carcinoma, gastrointestinal stromal tumors, multiple myeloma, uterine cancer, a sarcoma, kidney cancer, ocular cancer, pancreatic cancer, and a germ cell cancer (e.g., ovarian germ cell cancer). In certain embodiments, the cancer may be selected from leukemia, breast cancer, lung cancer, pancreatic cancer, endometrial cancer, ovarian cancer, prostate cancer, cervical cancer, brain cancer, skin cancer, colorectal cancer, gastric cancer, head and neck cancer, and leukemia. In certain embodiments, the cancer is selected from leukemia, breast cancer, cervical cancer, colorectal cancer, lung cancer, pancreatic cancer, prostate cancer, gastric cancer, head and neck cancer, endometrial cancer and ovarian cancer.

In certain embodiments, a fusion protein or expression vector of the disclosure is administered to decrease levels of one or more cytokines in a subject in need thereof (e.g., a subject with an inflammatory condition). In certain embodiments, a disclosed fusion protein or expression vector can be used to treat an inflammatory condition in a subject (e.g., a human subject), which can be accomplished by administering an effective amount of the fusion protein or expression vector to the subject.

As used herein, an inflammatory condition is a disease or condition characterized, in whole or in part, by inflammation or an inflammatory response in the patient. Inflammatory conditions treatable using the fusion proteins or expression vectors of the invention may be characterized, for example, based on the primary tissue affected, the mechanism of action underlying the condition, or the portion of the immune system that is misregulated or overactive. In certain embodiments, examples of inflammatory conditions that may be treated include inflammation of the lungs (e.g., asthma, adult respiratory distress syndrome, bronchitis, pulmonary inflammation, pulmonary fibrosis, and cystic fibrosis), joints (e.g., rheumatoid arthritis, rheumatoid spondylitis, juvenile rheumatoid arthritis, osteoarthritis, gouty arthritis and other arthritic conditions), connective tissue, eyes (e.g., uveitis (including iritis), conjunctivitis, scleritis, and keratoconjunctivitis sicca), nose, bowel (e.g., Crohn's disease, ulcerative colitis, inflammatory bowel disease, inflammatory bowel syndrome, and distal proctitis), kidney (e.g., glomerulonephritis, interstitial nephritis, lupus nephritis, nephritis secondary to Wegener's disease, acute renal failure secondary to acute nephritis, Goodpasture's syndrome, post-obstructive syndrome and tubular ischemia), liver (e.g., hepatitis (arising from viral infection, autoimmune responses, drug treatments, toxins, environmental agents, or as a secondary consequence of a primary disorder), obesity, biliary atresia, primary biliary cirrhosis and primary sclerosing cholangitis), skin (e.g., psoriasis, eczema, and dermatitis, e. g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), central nervous system (e.g., multiple sclerosis and neurodegenerative diseases such as Alzheimer's disease, Parkinson's disease or dementia associated with HIV infection), vascular system (e.g. coronary infarct damage, peripheral vascular disease, myocarditis, vasculitis, revascularization of stenosis, atherosclerosis, and vascular disease associated with Type II diabetes), endocrine system (e.g., autoimmune thyroiditis (Hashimoto's disease), Type I diabetes, inflammation in liver and adipose tissue associated with Type II diabetes, and acute and chronic inflammation of the adrenal cortex) heart, or adipose tissue. The disclosure contemplates that some inflammatory conditions involve inflammation in multiple tissues. Moreover, the disclosure contemplates that some inflammatory conditions may fall into multiple categories. In certain embodiments, the inflammatory condition is an autoimmune disease. Exemplary autoimmune diseases include, but are not limited to, rheumatoid arthritis, psoriasis (including plaque psoriasis), psoriatic arthritis, ankylosing spondylitis, ulcerative colitis, multiple sclerosis, lupus, alopecia, autoimmune pancreatitis, Celiac disease, Behcet's disease, Cushing syndrome, and Grave's disease. In certain embodiments, the inflammatory condition is a rheumatoid disorder. Exemplary rheumatoid disorders include, but are not limited to, rheumatoid arthritis, juvenile arthritis, bursitis, spondylitis, gout, scleroderma, Still's disease, and vasculitis. It is noted that certain categories of conditions overlap. For example, rheumatoid arthritis is an inflammatory rheumatoid disorder, an inflammatory joint disorder, and an autoimmune disorder.

The term "effective amount" as used herein refers to the amount of an active component (e.g., the amount of a fusion protein or expression vector of the present invention) sufficient to effect beneficial or desired results. An effective amount can be administered in one or more administrations, applications or dosages and is not intended to be limited to a particular formulation or administration route.

In certain embodiments, a therapeutically effective amount of a fusion protein is in the range of 0.1 mg/kg to 100 mg/kg, e.g., 1 mg/kg to 100 mg/kg, 1 mg/kg to 10 mg/kg, 1 mg/kg to 5 mg/kg, 10 mg/kg, 7.5 mg/kg, 5 mg/kg, or 2.5 mg/kg. In certain embodiments, a therapeutically effective amount of an expression vector, e.g., a recombinant virus, is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the fusion protein or expression vector, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. A preferred route of administration is parenteral, e.g., intravenous infusion. Formulation of fusion protein- or expression vector-based drugs is within ordinary skill in the art. In some embodiments, a fusion protein or expression vector is lyophilized, and then reconstituted in buffered saline, at the time of administration.

For therapeutic use, a fusion protein or expression vector preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing fusion proteins or expression vectors disclosed herein can be presented in a dosage unit form and can be prepared by any suitable method. A pharmaceutical composition should be formulated to be compatible with its intended route of administration. Examples of routes of administration are intravenous (IV), intradermal, inhalation, intraocular, intranasal, transdermal, topical, transmucosal, and rectal administration.

A preferred route of administration for fusion proteins is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS).

The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution. In certain embodiments, a delivery vehicle (e.g., a recombinant virus) and/or a therapeutic agent of the invention is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab (Bavencio®, EMD Serono), and BMS 936559 (Bristol Myers Squibb Co.).

The term administered "in combination," as used herein, is understood to mean that two (or more) different treatments are delivered to the subject during the course of the subject's affliction with the disorder, such that the effects of the treatments on the subject overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where compositions, devices, and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1: IL-10RA Fusion Protein Plasmid Construction

This Example describes the production of plasmids and viral expression vectors that encode IL-10RA fusion proteins.

Nucleotide sequences encoding a series of human IL-10RA fusion proteins were generated. A first fusion protein, hIL-10R-IgG1 (SEQ ID NO: 58), included residues 1-229 of human IL-10RA (ending in SLTRQ), immediately followed by residues 84-330 of the human IgG1 sequence, (beginning with NVNHK). A second fusion protein, hIL-10R-Fc (SEQ ID NO: 48), included residues 1-235 of human IL-10RA (ending in FTVTN), immediately followed by residues 104-324 of human IgG1 (beginning at DKTHT). Details of the fusion proteins are shown in TABLE 3.

TABLE 3

| Fusion Protein | hIL-10RA Residues | hIgG1 Residues | hIL-10RA-hIgG1 Junction |
|---|---|---|---|
| hIL-10R-IgG1 | 1-229 | 84-330 | SLTRQ-NVNEIKPSNTKVDKRVEPKSCDKT |
| hIL-10R-Fc | 1-235 | 104-324 | SLTRQYFTVTN-DKTHT |

Nucleotide sequences encoding the fusion proteins were cloned into plasmids for downstream applications as appropriate. In particular, recombinant adenoviral vectors were generated that expressed no transgene, hIL-10R-IgG1, or hIL-10RA-Fc.

Example 2: IL-10R Fusion Protein Activity

A549 cells (human lung cancer cells) were infected with viral vectors expressing no transgene, hIL-10R-IgG1, or hIL-10RA-Fc, as described in Example 1, at 10 MOI, and cultured for four days. Conditioned media from the cell culture was collected and THP-1 cells (human leukemic monocytes) were suspended in the conditioned media at $5 \times 10^6$ cells/ml. Cells were either treated with human IL-10 at 50 ng/ml at 37° C. for 30 minutes or kept as controls. To assay for IL-10 activity, extracted cellular protein from the THP-1 cells was probed by Western blot for phosphorylated Stat3. Total Stat3 was used as a loading control.

IL-10 induced Stat3 phosphorylation in THP-1 cells cultured in conditioned media from cells infected with viral vectors expressing no transgene or hIL-10RA-Fc. However, IL-10 did not induce Stat3 phosphorylation in THP-1 cells cultured in conditioned media from cells infected with hIL10R-IgG-expressing virus. These results demonstrate that the hIL-10R-IgG1 fusion protein blocked IL-10 from activating the Stat3 signaling cascade.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated fusion protein comprising, in an N- to C-terminal orientation:
   (i) a soluble portion of an extracellular domain of a human IL-10 receptor subunit alpha, wherein the soluble portion of an extracellular domain of a human IL-10 receptor has greater than 95% sequence identity to amino acid residues 22-229 of SEQ ID NO: 12;
   (ii) an amino acid linker;
   (iii) an immunoglobulin (Ig) hinge region; and
   (iv) an immunoglobulin (Ig) Fc domain;
wherein the linker consists of 10 to 40 amino acid residues, wherein the linker is a sequence derived from an endogenous human protein, wherein the Ig hinge region and the Ig Fe domain together comprise an amino acid sequence having greater than 95% identity to SEQ ID NOs: 13-21, and wherein the linker comprises a sequence derived from a human protein selected from albumin and casein, or comprises a C-terminal portion of an immunoglobulin (Ig) CH1 domain having greater than 95% sequence identity to an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 53, SEQ ID NO: 57, SEQ II) NO: 59, SEQ ID NO: 60, SEQ ID NO: 61, SEQ II) NO: 62, and SEQ ID NO: 63.

2. The isolated fusion protein of claim 1, wherein the linker comprises a sequence derived from a human protein selected from albumin and casein, or comprises a C-terminal portion of an immunoglobulin (Ig) CH1 domain having greater than 98% sequence identity to an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 53, SEQ ID NO: 57, SEQ ID NO: 59, SEQ ID NO: 60, SEQ ID NO: 61, SEQ ID NO: 62, and SEQ ID NO: 63.

3. The isolated fusion protein of claim 1, wherein the linker comprises an amino acid sequence which is proteolytically stable in a mammal or plant or comprises a cleavage site.

4. The isolated fusion protein of claim 1, wherein the soluble portion of an extracellular domain of an IL-10 receptor comprises the amino acid sequence of SEQ ID NO: 12 or amino acid residues 22-229 of SEQ ID NO: 12.

5. The isolated fusion protein of claim 1, wherein the Ig Fc domain and Ig hinge region together comprise an amino acid sequence selected from SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

6. The isolated fusion protein of claim 2, wherein the fusion protein has greater than 95% sequence identity to an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ NO: 33, SEQ ID NO: 55, and SEQ ID NO: 58.

7. An isolated nucleic acid comprising a nucleotide sequence encoding the fusion protein of claim 1.

8. An expression vector comprising the nucleic acid of claim 7.

9. A host cell comprising the expression vector of any one of claim 8.

10. A method of producing a fusion protein comprising:
    (a) growing the host cell of claim 9 under conditions to express the fusion protein; and
    (b) purifying the fusion protein.

11. A pharmaceutical composition comprising: (i) the fusion protein of claim 1; and (ii) at least one pharmaceutically acceptable carrier or diluent.

* * * * *

SEQUENCE LISTING

```
<160> NUMBER OF SEQ ID NOS: 64

<210> SEQ ID NO 1
<211> LENGTH: 12
<212> TYPE: PRT
<213> ORGANISM: Homo sapiens

<400> SEQUENCE: 1

Lys Pro Ser Asn Thr Lys Val Asp Lys Lys Val Glu
1               5                   10

<210> SEQ ID NO 2
<211> LENGTH: 12
<212> TYPE: PRT
<213> ORGANISM: Homo sapiens

<400> SEQUENCE: 2

Lys Pro Ser Asn Thr Lys Val Asp Lys Thr Val Glu
1               5                   10

<210> SEQ ID NO 3
<211> LENGTH: 12
<212> TYPE: PRT
<213> ORGANISM: Homo sapiens

<400> SEQUENCE: 3

Lys Pro Ser Asn Thr Lys Val Asp Lys Arg Val Glu
1               5                   10

<210> SEQ ID NO 4
<211> LENGTH: 12
<212> TYPE: PRT
```

```
<213> ORGANISM: Homo sapiens

<400> SEQUENCE: 4

Lys Pro Ser Asn Thr Lys Val Asp Lys Arg Val Glu
1               5                   10

<210> SEQ ID NO 5
<211> LENGTH: 12
<212> TYPE: PRT
<213> ORGANISM: Homo sapiens

<400> SEQUENCE: 5

Val Lys His Tyr Thr Asn Pro Ser Gln Asp Val Thr
1               5                   10

<210> SEQ ID NO 6
<211> LENGTH: 12
<212> TYPE: PRT
<213> ORGANISM: Homo sapiens

<400> SEQUENCE: 6

Val Lys His Tyr Thr Asn Pro Ser Gln Asp Val Thr
1               5                   10

<210> SEQ ID NO 7
<211> LENGTH: 10
<212> TYPE: PRT
<213> ORGANISM: Homo sapiens

<400> SEQUENCE: 7

Thr Ala Ser Lys Ser Lys Lys Glu Ile Phe
1               5                   10

<210> SEQ ID NO 8
<211> LENGTH: 14
<212> TYPE: PRT
<213> ORGANISM: Homo sapiens

<400> SEQUENCE: 8

Thr Pro Ser Ser Thr Asp Trp Val Asp Asn Lys Thr Phe Ser
1               5                   10

<210> SEQ ID NO 9
<211> LENGTH: 13
<212> TYPE: PRT
<213> ORGANISM: Homo sapiens

<400> SEQUENCE: 9

Val Gln His Pro Asn Gly Asn Lys Glu Lys Asn Val Pro
1               5                   10

<210> SEQ ID NO 10
<211> LENGTH: 13
<212> TYPE: PRT
<213> ORGANISM: Homo sapiens

<400> SEQUENCE: 10

Val Gln His Pro Asn Gly Asn Lys Glu Lys Asn Val Pro
1               5                   10

<210> SEQ ID NO 11
<211> LENGTH: 12
<212> TYPE: PRT
<213> ORGANISM: Homo sapiens
```

<400> SEQUENCE: 11

Arg Glu Lys Gln Thr Asp Glu Ile Lys Asp Thr Arg
1               5                   10

<210> SEQ ID NO 12
<211> LENGTH: 229
<212> TYPE: PRT
<213> ORGANISM: Homo sapiens

<400> SEQUENCE: 12

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln
225

<210> SEQ ID NO 13
<211> LENGTH: 231
<212> TYPE: PRT
<213> ORGANISM: Homo sapiens

<400> SEQUENCE: 13

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr

```
             65                  70                  75                  80
Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 14
<211> LENGTH: 227
<212> TYPE: PRT
<213> ORGANISM: Homo sapiens

<400> SEQUENCE: 14

Arg Lys Cys Cys Val Glu Cys Pro Pro Cys Pro Ala Pro Pro Val Ala
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Gln Phe Asn Trp Tyr Val Asp Gly Val Glu Val
        50                  55                  60

His Asn Ala Lys Thr Lys Pro Arg Glu Glu Gln Phe Asn Ser Thr Phe
65                  70                  75                  80

Arg Val Val Ser Val Leu Thr Val Val His Gln Asp Trp Leu Asn Gly
                85                  90                  95

Lys Glu Tyr Lys Cys Lys Val Ser Asn Lys Gly Leu Pro Ala Pro Ile
                100                 105                 110

Glu Lys Thr Ile Ser Lys Thr Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ser Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly Lys
225

<210> SEQ ID NO 15
<211> LENGTH: 278
<212> TYPE: PRT
<213> ORGANISM: Homo sapiens

<400> SEQUENCE: 15

Leu Lys Thr Pro Leu Gly Asp Thr Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro Ala Pro Glu
    50                  55                  60

Leu Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Gln Phe Lys Trp Tyr Val Asp Gly
            100                 105                 110

Val Glu Val His Asn Ala Lys Thr Lys Pro Arg Glu Glu Gln Tyr Asn
        115                 120                 125

Ser Thr Phe Arg Val Val Ser Val Leu Thr Val Leu His Gln Asp Trp
    130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Thr Lys Gly Gln Pro Arg Glu
                165                 170                 175

Pro Gln Val Tyr Thr Leu Pro Pro Ser Arg Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Ser Gly Gln Pro Glu Asn Asn Tyr Asn Thr
    210                 215                 220

Thr Pro Pro Met Leu Asp Ser Asp Gly Ser Phe Phe Leu Tyr Ser Lys
225                 230                 235                 240

Leu Thr Val Asp Lys Ser Arg Trp Gln Gln Gly Asn Ile Phe Ser Cys
                245                 250                 255

Ser Val Met His Glu Ala Leu His Asn Arg Phe Thr Gln Lys Ser Leu
            260                 265                 270

Ser Leu Ser Pro Gly Lys
        275

<210> SEQ ID NO 16
<211> LENGTH: 228
<212> TYPE: PRT
<213> ORGANISM: Homo sapiens

<400> SEQUENCE: 16

Ser Lys Tyr Gly Pro Pro Cys Pro Ser Cys Pro Ala Pro Glu Phe Leu
1               5                   10                  15
```

```
Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

Gln Glu Asp Pro Glu Val Gln Phe Asn Trp Tyr Val Asp Gly Val Glu
     50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 17
<211> LENGTH: 255
<212> TYPE: PRT
<213> ORGANISM: Homo sapiens

<400> SEQUENCE: 17

Val Pro Cys Pro Val Pro Ser Thr Pro Pro Thr Pro Ser Pro Ser Thr
1               5                   10                  15

Pro Pro Thr Pro Ser Pro Ser Cys Cys His Pro Arg Leu Ser Leu His
            20                  25                  30

Arg Pro Ala Leu Glu Asp Leu Leu Leu Gly Ser Glu Ala Asn Leu Thr
        35                  40                  45

Cys Thr Leu Thr Gly Leu Arg Asp Ala Ser Gly Val Thr Phe Thr Trp
    50                  55                  60

Thr Pro Ser Ser Gly Lys Ser Ala Val Gln Gly Pro Pro Glu Arg Asp
65                  70                  75                  80

Leu Cys Gly Cys Tyr Ser Val Ser Ser Val Leu Pro Gly Cys Ala Glu
                85                  90                  95

Pro Trp Asn His Gly Lys Thr Phe Thr Cys Thr Ala Ala Tyr Pro Glu
            100                 105                 110

Ser Lys Thr Pro Leu Thr Ala Thr Leu Ser Lys Ser Gly Asn Thr Phe
        115                 120                 125

Arg Pro Glu Val His Leu Leu Pro Pro Ser Glu Glu Leu Ala Leu
    130                 135                 140

Asn Glu Leu Val Thr Leu Thr Cys Leu Ala Arg Gly Phe Ser Pro Lys
145                 150                 155                 160
```

Asp Val Leu Val Arg Trp Leu Gln Gly Ser Gln Glu Leu Pro Arg Glu
            165                 170                 175

Lys Tyr Leu Thr Trp Ala Ser Arg Gln Glu Pro Ser Gln Gly Thr Thr
            180                 185                 190

Thr Phe Ala Val Thr Ser Ile Leu Arg Val Ala Ala Glu Asp Trp Lys
            195                 200                 205

Lys Gly Asp Thr Phe Ser Cys Met Val Gly His Glu Ala Leu Pro Leu
        210                 215                 220

Ala Phe Thr Gln Lys Thr Ile Asp Arg Leu Ala Gly Lys Pro Thr His
225                 230                 235                 240

Val Asn Val Ser Val Val Met Ala Glu Val Asp Gly Thr Cys Tyr
            245                 250                 255

<210> SEQ ID NO 18
<211> LENGTH: 242
<212> TYPE: PRT
<213> ORGANISM: Homo sapiens

<400> SEQUENCE: 18

Val Pro Cys Pro Val Pro Pro Pro Pro Cys Cys His Pro Arg Leu
1               5                   10                  15

Ser Leu His Arg Pro Ala Leu Glu Asp Leu Leu Leu Gly Ser Glu Ala
            20                  25                  30

Asn Leu Thr Cys Thr Leu Thr Gly Leu Arg Asp Ala Ser Gly Ala Thr
        35                  40                  45

Phe Thr Trp Thr Pro Ser Ser Gly Lys Ser Ala Val Gln Gly Pro Pro
    50                  55                  60

Glu Arg Asp Leu Cys Gly Cys Tyr Ser Val Ser Ser Val Leu Pro Gly
65                  70                  75                  80

Cys Ala Gln Pro Trp Asn His Gly Glu Thr Phe Thr Cys Thr Ala Ala
                85                  90                  95

His Pro Glu Leu Lys Thr Pro Leu Thr Ala Asn Ile Thr Lys Ser Gly
            100                 105                 110

Asn Thr Phe Arg Pro Glu Val His Leu Leu Pro Pro Pro Ser Glu Glu
        115                 120                 125

Leu Ala Leu Asn Glu Leu Val Thr Leu Thr Cys Leu Ala Arg Gly Phe
    130                 135                 140

Ser Pro Lys Asp Val Leu Val Arg Trp Leu Gln Gly Ser Gln Glu Leu
145                 150                 155                 160

Pro Arg Glu Lys Tyr Leu Thr Trp Ala Ser Arg Gln Glu Pro Ser Gln
                165                 170                 175

Gly Thr Thr Thr Phe Ala Val Thr Ser Ile Leu Arg Val Ala Ala Glu
            180                 185                 190

Asp Trp Lys Lys Gly Asp Thr Phe Ser Cys Met Val Gly His Glu Ala
        195                 200                 205

Leu Pro Leu Ala Phe Thr Gln Lys Thr Ile Asp Arg Met Ala Gly Lys
    210                 215                 220

Pro Thr His Val Asn Val Ser Val Val Met Ala Glu Val Asp Gly Thr
225                 230                 235                 240

Cys Tyr

<210> SEQ ID NO 19
<211> LENGTH: 286
<212> TYPE: PRT
<213> ORGANISM: Homo sapiens

<400> SEQUENCE: 19

Arg Trp Pro Glu Ser Pro Lys Ala Gln Ala Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
                35                  40                  45

Glu Lys Glu Glu Gln Glu Gly Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His Gly Pro Met Lys
            275                 280                 285

<210> SEQ ID NO 20
<211> LENGTH: 325
<212> TYPE: PRT
<213> ORGANISM: Homo sapiens

<400> SEQUENCE: 20

Val Cys Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
            35                  40                  45

Asp Gly Gln Val Met Asp Val Asp Leu Ser Thr Ala Ser Thr Thr Gln
        50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala Asp Ser Asn Pro Arg
            100                 105                 110

Gly Val Ser Ala Tyr Leu Ser Arg Pro Ser Pro Phe Asp Leu Phe Ile
        115                 120                 125

Arg Lys Ser Pro Thr Ile Thr Cys Leu Val Val Asp Leu Ala Pro Ser
130                 135                 140

Lys Gly Thr Val Asn Leu Thr Trp Ser Arg Ala Ser Gly Lys Pro Val
145                 150                 155                 160

Asn His Ser Thr Arg Lys Glu Lys Gln Arg Asn Gly Thr Leu Thr
                165                 170                 175

Val Thr Ser Thr Leu Pro Val Gly Thr Arg Asp Trp Ile Glu Gly Glu
            180                 185                 190

Thr Tyr Gln Cys Arg Val Thr His Pro His Leu Pro Arg Ala Leu Met
        195                 200                 205

Arg Ser Thr Thr Lys Thr Ser Gly Pro Arg Ala Ala Pro Glu Val Tyr
210                 215                 220

Ala Phe Ala Thr Pro Glu Trp Pro Gly Ser Arg Asp Lys Arg Thr Leu
225                 230                 235                 240

Ala Cys Leu Ile Gln Asn Phe Met Pro Glu Asp Ile Ser Val Gln Trp
                245                 250                 255

Leu His Asn Glu Val Gln Leu Pro Asp Ala Arg His Ser Thr Thr Gln
            260                 265                 270

Pro Arg Lys Thr Lys Gly Ser Gly Phe Val Phe Ser Arg Leu Glu
        275                 280                 285

Val Thr Arg Ala Glu Trp Glu Gln Lys Asp Glu Phe Ile Cys Arg Ala
290                 295                 300

Val His Glu Ala Ala Ser Pro Ser Gln Thr Val Gln Arg Ala Val Ser
305                 310                 315                 320

Val Asn Pro Gly Lys
                325

<210> SEQ ID NO 21
<211> LENGTH: 351
<212> TYPE: PRT
<213> ORGANISM: Homo sapiens

<400> SEQUENCE: 21

Leu Pro Val Ile Ala Glu Leu Pro Pro Lys Val Ser Val Phe Val Pro
1               5                   10                  15

Pro Arg Asp Gly Phe Phe Gly Asn Pro Arg Lys Ser Lys Leu Ile Cys
            20                  25                  30

Gln Ala Thr Gly Phe Ser Pro Arg Gln Ile Gln Val Ser Trp Leu Arg
        35                  40                  45

Glu Gly Lys Gln Val Gly Ser Gly Val Thr Thr Asp Gln Val Gln Ala
    50                  55                  60

Glu Ala Lys Glu Ser Gly Pro Thr Thr Tyr Lys Val Thr Ser Thr Leu
65                  70                  75                  80

Thr Ile Lys Glu Ser Asp Trp Leu Ser Gln Ser Met Phe Thr Cys Arg
                85                  90                  95

Val Asp His Arg Gly Leu Thr Phe Gln Gln Asn Ala Ser Ser Met Cys
            100                 105                 110

Val Pro Asp Gln Asp Thr Ala Ile Arg Val Phe Ala Ile Pro Pro Ser

-continued

```
            115                 120                 125
Phe Ala Ser Ile Phe Leu Thr Lys Ser Thr Lys Leu Thr Cys Leu Val
        130                 135                 140
Thr Asp Leu Thr Thr Tyr Asp Ser Val Thr Ile Ser Trp Thr Arg Gln
145                 150                 155                 160
Asn Gly Glu Ala Val Lys Thr His Thr Asn Ile Ser Glu Ser His Pro
                165                 170                 175
Asn Ala Thr Phe Ser Ala Val Gly Glu Ala Ser Ile Cys Glu Asp Asp
                180                 185                 190
Trp Asn Ser Gly Glu Arg Phe Thr Cys Thr Val Thr His Thr Asp Leu
                195                 200                 205
Pro Ser Pro Leu Lys Gln Thr Ile Ser Arg Pro Lys Gly Val Ala Leu
        210                 215                 220
His Arg Pro Asp Val Tyr Leu Leu Pro Ala Arg Glu Gln Leu Asn
225                 230                 235                 240
Leu Arg Glu Ser Ala Thr Ile Thr Cys Leu Val Thr Gly Phe Ser Pro
                245                 250                 255
Ala Asp Val Phe Val Gln Trp Met Gln Arg Gly Gln Pro Leu Ser Pro
                260                 265                 270
Glu Lys Tyr Val Thr Ser Ala Pro Met Pro Glu Pro Gln Ala Pro Gly
                275                 280                 285
Arg Tyr Phe Ala His Ser Ile Leu Thr Val Ser Glu Glu Trp Asn
        290                 295                 300
Thr Gly Glu Thr Tyr Thr Cys Val Val Ala His Glu Ala Leu Pro Asn
305                 310                 315                 320
Arg Val Thr Glu Arg Thr Val Asp Lys Ser Thr Gly Lys Pro Thr Leu
                325                 330                 335
Tyr Asn Val Ser Leu Val Met Ser Asp Thr Ala Gly Thr Cys Tyr
        340                 345                 350

<210> SEQ ID NO 22
<211> LENGTH: 472
<212> TYPE: PRT
<213> ORGANISM: Artificial Sequence
<220> FEATURE:
<223> OTHER INFORMATION: Synthetic

<400> SEQUENCE: 22

Met Leu Pro Cys Leu Val Val Leu Leu Ala Ala Leu Leu Ser Leu Arg
1               5                   10                  15
Leu Gly Ser Asp Ala His Gly Thr Glu Leu Pro Ser Pro Pro Ser Val
                20                  25                  30
Trp Phe Glu Ala Glu Phe Phe His His Ile Leu His Trp Thr Pro Ile
                35                  40                  45
Pro Asn Gln Ser Glu Ser Thr Cys Tyr Glu Val Ala Leu Leu Arg Tyr
        50                  55                  60
Gly Ile Glu Ser Trp Asn Ser Ile Ser Asn Cys Ser Gln Thr Leu Ser
65                  70                  75                  80
Tyr Asp Leu Thr Ala Val Thr Leu Asp Leu Tyr His Ser Asn Gly Tyr
                85                  90                  95
Arg Ala Arg Val Arg Ala Val Asp Gly Ser Arg His Ser Asn Trp Thr
                100                 105                 110
Val Thr Asn Thr Arg Phe Ser Val Asp Glu Val Thr Leu Thr Val Gly
                115                 120                 125
Ser Val Asn Leu Glu Ile His Asn Gly Phe Ile Leu Gly Lys Ile Gln
```

```
                130                 135                 140
Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
                195                 200                 205

Val Ala Ser Arg Ser Asn Lys Gly Met Trp Ser Lys Glu Glu Cys Ile
        210                 215                 220

Ser Leu Thr Arg Gln Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
                370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 23
<211> LENGTH: 468
<212> TYPE: PRT
<213> ORGANISM: Artificial Sequence
<220> FEATURE:
<223> OTHER INFORMATION: Synthetic

<400> SEQUENCE: 23

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
```

```
                20                  25                  30
Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
 50                  55                  60

Gly Ile Glu Ser Trp Asn Ser Ile Ser Asn Cys Ser Gln Thr Leu Ser
 65                  70                  75                  80

Tyr Asp Leu Thr Ala Val Thr Leu Asp Leu Tyr His Ser Asn Gly Tyr
            85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
            115                 120                 125

Ser Val Asn Leu Glu Ile His Asn Gly Phe Ile Leu Gly Lys Ile Gln
            130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
            165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Ile
            210                 215                 220

Ser Leu Thr Arg Gln Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Gln Phe Asn Trp Tyr Val Asp Gly Val Glu
            290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
            325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ser Val
385                 390                 395                 400

Glu Trp Glu Ser Asn Gly Gln Pro Glu Asn Asn Tyr Lys Thr Thr Pro
            405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445
```

-continued

Met His Glu Ala Leu His Asn His Tyr Thr Gln Lys Ser Leu Ser Leu
    450                 455                 460

Ser Pro Gly Lys
465

<210> SEQ ID NO 24
<211> LENGTH: 519
<212> TYPE: PRT
<213> ORGANISM: Artificial Sequence
<220> FEATURE:
<223> OTHER INFORMATION: Synthetic

<400> SEQUENCE: 24

Met Leu Pro Cys Leu Val Val Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Lys Pro Ser Asn Thr Lys Val Asp Lys Arg Val
225                 230                 235                 240

Glu Leu Lys Thr Pro Leu Gly Asp Thr Thr His Thr Cys Pro Arg Cys
                245                 250                 255

Pro Glu Pro Lys Ser Cys Asp Thr Pro Pro Cys Pro Arg Cys Pro
            260                 265                 270

Glu Pro Lys Ser Cys Asp Thr Pro Pro Cys Pro Arg Cys Pro Glu
        275                 280                 285

Pro Lys Ser Cys Asp Thr Pro Pro Cys Pro Arg Cys Pro Ala Pro
    290                 295                 300

Glu Leu Leu Gly Gly Pro Ser Val Phe Leu Phe Pro Pro Lys Pro Lys
305                 310                 315                 320

Asp Thr Leu Met Ile Ser Arg Thr Pro Glu Val Thr Cys Val Val Val
                325                 330                 335

```
Asp Val Ser His Glu Asp Pro Glu Val Gln Phe Lys Trp Tyr Val Asp
            340                 345                 350

Gly Val Glu Val His Asn Ala Lys Thr Lys Pro Arg Glu Glu Gln Tyr
        355                 360                 365

Asn Ser Thr Phe Arg Val Ser Val Leu Thr Val Leu His Gln Asp
    370                 375                 380

Trp Leu Asn Gly Lys Glu Tyr Lys Cys Lys Val Ser Asn Lys Ala Leu
385                 390                 395                 400

Pro Ala Pro Ile Glu Lys Thr Ile Ser Lys Thr Lys Gly Gln Pro Arg
                405                 410                 415

Glu Pro Gln Val Tyr Thr Leu Pro Pro Ser Arg Glu Glu Met Thr Lys
            420                 425                 430

Asn Gln Val Ser Leu Thr Cys Leu Val Lys Gly Phe Tyr Pro Ser Asp
        435                 440                 445

Ile Ala Val Glu Trp Glu Ser Ser Gly Gln Pro Glu Asn Asn Tyr Asn
    450                 455                 460

Thr Thr Pro Pro Met Leu Asp Ser Asp Gly Ser Phe Phe Leu Tyr Ser
465                 470                 475                 480

Lys Leu Thr Val Asp Lys Ser Arg Trp Gln Gln Gly Asn Ile Phe Ser
                485                 490                 495

Cys Ser Val Met His Glu Ala Leu His Asn Arg Phe Thr Gln Lys Ser
            500                 505                 510

Leu Ser Leu Ser Pro Gly Lys
        515

<210> SEQ ID NO 25
<211> LENGTH: 469
<212> TYPE: PRT
<213> ORGANISM: Artificial Sequence
<220> FEATURE:
<223> OTHER INFORMATION: Synthetic

<400> SEQUENCE: 25

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175
```

```
Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
210                 215                 220

Ser Leu Thr Arg Gln Lys Pro Ser Asn Thr Lys Val Asp Lys Arg Val
225                 230                 235                 240

Glu Ser Lys Tyr Gly Pro Pro Cys Pro Ser Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
450                 455                 460

Leu Ser Leu Gly Lys
465

<210> SEQ ID NO 26
<211> LENGTH: 496
<212> TYPE: PRT
<213> ORGANISM: Artificial Sequence
<220> FEATURE:
<223> OTHER INFORMATION: Synthetic

<400> SEQUENCE: 26

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60
```

```
Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Val Lys His Tyr Thr Asn Pro Ser Gln Asp Val
225                 230                 235                 240

Thr Val Pro Cys Pro Val Pro Ser Thr Pro Thr Pro Ser Pro Ser
                245                 250                 255

Thr Pro Pro Thr Pro Ser Pro Ser Cys Cys His Pro Arg Leu Ser Leu
            260                 265                 270

His Arg Pro Ala Leu Glu Asp Leu Leu Leu Gly Ser Glu Ala Asn Leu
        275                 280                 285

Thr Cys Thr Leu Thr Gly Leu Arg Asp Ala Ser Gly Val Thr Phe Thr
    290                 295                 300

Trp Thr Pro Ser Ser Gly Lys Ser Ala Val Gln Gly Pro Pro Glu Arg
305                 310                 315                 320

Asp Leu Cys Gly Cys Tyr Ser Val Ser Ser Val Leu Pro Gly Cys Ala
                325                 330                 335

Glu Pro Trp Asn His Gly Lys Thr Phe Thr Cys Thr Ala Ala Tyr Pro
            340                 345                 350

Glu Ser Lys Thr Pro Leu Thr Ala Thr Leu Ser Lys Ser Gly Asn Thr
        355                 360                 365

Phe Arg Pro Glu Val His Leu Leu Pro Pro Ser Glu Glu Leu Ala
    370                 375                 380

Leu Asn Glu Leu Val Thr Leu Thr Cys Leu Ala Arg Gly Phe Ser Pro
385                 390                 395                 400

Lys Asp Val Leu Val Arg Trp Leu Gln Gly Ser Gln Glu Leu Pro Arg
                405                 410                 415

Glu Lys Tyr Leu Thr Trp Ala Ser Arg Gln Glu Pro Ser Gln Gly Thr
            420                 425                 430

Thr Thr Phe Ala Val Thr Ser Ile Leu Arg Val Ala Ala Glu Asp Trp
        435                 440                 445

Lys Lys Gly Asp Thr Phe Ser Cys Met Val Gly His Glu Ala Leu Pro
    450                 455                 460

Leu Ala Phe Thr Gln Lys Thr Ile Asp Arg Leu Ala Gly Lys Pro Thr
465                 470                 475                 480
```

His Val Asn Val Ser Val Met Ala Glu Val Asp Gly Thr Cys Tyr
            485                 490                 495

<210> SEQ ID NO 27
<211> LENGTH: 483
<212> TYPE: PRT
<213> ORGANISM: Artificial Sequence
<220> FEATURE:
<223> OTHER INFORMATION: Synthetic

<400> SEQUENCE: 27

Met Leu Pro Cys Leu Val Val Leu Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Val Lys His Tyr Thr Asn Pro Ser Gln Asp Val
225                 230                 235                 240

Thr Val Pro Cys Pro Val Pro Pro Pro Cys Cys His Pro Arg
                245                 250                 255

Leu Ser Leu His Arg Pro Ala Leu Glu Asp Leu Leu Gly Ser Glu
            260                 265                 270

Ala Asn Leu Thr Cys Thr Leu Thr Gly Leu Arg Asp Ala Ser Gly Ala
        275                 280                 285

Thr Phe Thr Trp Thr Pro Ser Ser Gly Lys Ser Ala Val Gln Gly Pro
    290                 295                 300

Pro Glu Arg Asp Leu Cys Gly Cys Tyr Ser Val Ser Ser Val Leu Pro
305                 310                 315                 320

Gly Cys Ala Gln Pro Trp Asn His Gly Glu Thr Phe Thr Cys Thr Ala
                325                 330                 335

Ala His Pro Glu Leu Lys Thr Pro Leu Thr Ala Asn Ile Thr Lys Ser
            340                 345                 350

```
Gly Asn Thr Phe Arg Pro Glu Val His Leu Leu Pro Pro Ser Glu
            355                 360                 365

Glu Leu Ala Leu Asn Glu Leu Val Thr Leu Thr Cys Leu Ala Arg Gly
    370                 375                 380

Phe Ser Pro Lys Asp Val Leu Val Arg Trp Leu Gln Gly Ser Gln Glu
385                 390                 395                 400

Leu Pro Arg Glu Lys Tyr Leu Thr Trp Ala Ser Arg Gln Glu Pro Ser
                405                 410                 415

Gln Gly Thr Thr Thr Phe Ala Val Thr Ser Ile Leu Arg Val Ala Ala
            420                 425                 430

Glu Asp Trp Lys Lys Gly Asp Thr Phe Ser Cys Met Val Gly His Glu
    435                 440                 445

Ala Leu Pro Leu Ala Phe Thr Gln Lys Thr Ile Asp Arg Met Ala Gly
    450                 455                 460

Lys Pro Thr His Val Asn Val Ser Val Val Met Ala Glu Val Asp Gly
465                 470                 475                 480

Thr Cys Tyr

<210> SEQ ID NO 28
<211> LENGTH: 525
<212> TYPE: PRT
<213> ORGANISM: Artificial Sequence
<220> FEATURE:
<223> OTHER INFORMATION: Synthetic

<400> SEQUENCE: 28

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Thr Ala Ser Lys Ser Lys Lys Glu Ile Phe Arg
```

```
            225                 230                 235                 240

Trp Pro Glu Ser Pro Lys Ala Gln Ala Ser Ser Val Pro Thr Ala Gln
                245                 250                 255

Pro Gln Ala Glu Gly Ser Leu Ala Lys Ala Thr Thr Ala Pro Ala Thr
            260                 265                 270

Thr Arg Asn Thr Gly Arg Gly Glu Lys Lys Lys Glu Lys Glu
            275                 280                 285

Lys Glu Glu Gln Glu Arg Glu Thr Lys Thr Pro Glu Cys Pro Ser
    290                 295                 300

His Thr Gln Pro Leu Gly Val Tyr Leu Leu Thr Pro Ala Val Gln Asp
305                 310                 315                 320

Leu Trp Leu Arg Asp Lys Ala Thr Phe Thr Cys Phe Val Val Gly Ser
                325                 330                 335

Asp Leu Lys Asp Ala His Leu Thr Trp Glu Val Ala Gly Lys Val Pro
            340                 345                 350

Thr Gly Gly Val Glu Glu Gly Leu Leu Glu Arg His Ser Asn Gly Ser
        355                 360                 365

Gln Ser Gln His Ser Arg Leu Thr Leu Pro Arg Ser Leu Trp Asn Ala
    370                 375                 380

Gly Thr Ser Val Thr Cys Thr Leu Asn His Pro Ser Leu Pro Pro Gln
385                 390                 395                 400

Arg Leu Met Ala Leu Arg Glu Pro Ala Ala Gln Ala Pro Val Lys Leu
                405                 410                 415

Ser Leu Asn Leu Leu Ala Ser Ser Asp Pro Pro Glu Ala Ala Ser Trp
            420                 425                 430

Leu Leu Cys Glu Val Ser Gly Phe Ser Pro Pro Asn Ile Leu Leu Met
        435                 440                 445

Trp Leu Glu Asp Gln Arg Glu Val Asn Thr Ser Gly Phe Ala Pro Ala
    450                 455                 460

Arg Pro Pro Pro Gln Pro Gly Ser Thr Thr Phe Trp Ala Trp Ser Val
465                 470                 475                 480

Leu Arg Val Pro Ala Pro Pro Ser Pro Gln Pro Ala Thr Tyr Thr Cys
                485                 490                 495

Val Val Ser His Glu Asp Ser Arg Thr Leu Leu Asn Ala Ser Arg Ser
            500                 505                 510

Leu Glu Val Ser Tyr Val Thr Asp His Gly Pro Met Lys
        515                 520                 525

<210> SEQ ID NO 29
<211> LENGTH: 568
<212> TYPE: PRT
<213> ORGANISM: Artificial Sequence
<220> FEATURE:
<223> OTHER INFORMATION: Synthetic

<400> SEQUENCE: 29

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
```

```
                65                  70                  75                  80

Tyr Asp Leu Thr Ala Val Thr Leu Asp Leu Tyr His Ser Asn Gly Tyr
                    85                  90                  95

Arg Ala Arg Val Arg Ala Val Asp Gly Ser Arg His Ser Asn Trp Thr
                    100                 105                 110

Val Thr Asn Thr Arg Phe Ser Val Asp Glu Val Thr Leu Thr Val Gly
                    115                 120                 125

Ser Val Asn Leu Glu Ile His Asn Gly Phe Ile Leu Gly Lys Ile Gln
                    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                    165                 170                 175

Asn Phe Thr Phe Thr His Lys Lys Val Lys His Glu Asn Phe Ser Leu
                    180                 185                 190

Leu Thr Ser Gly Glu Val Gly Glu Phe Cys Val Gln Val Lys Pro Ser
                    195                 200                 205

Val Ala Ser Arg Ser Asn Lys Gly Met Trp Ser Lys Glu Glu Cys Ile
            210                 215                 220

Ser Leu Thr Arg Gln Thr Pro Ser Ser Thr Asp Trp Val Asp Asn Lys
225                 230                 235                 240

Thr Phe Ser Val Cys Ser Arg Asp Phe Thr Pro Pro Thr Val Lys Ile
                    245                 250                 255

Leu Gln Ser Ser Cys Asp Gly Gly His Phe Pro Pro Thr Ile Gln
                    260                 265                 270

Leu Leu Cys Leu Val Ser Gly Tyr Thr Pro Gly Thr Ile Asn Ile Thr
            275                 280                 285

Trp Leu Glu Asp Gly Gln Val Met Asp Val Asp Leu Ser Thr Ala Ser
            290                 295                 300

Thr Thr Gln Glu Gly Glu Leu Ala Ser Thr Gln Ser Glu Leu Thr Leu
305                 310                 315                 320

Ser Gln Lys His Trp Leu Ser Asp Arg Thr Tyr Thr Cys Gln Val Thr
                    325                 330                 335

Tyr Gln Gly His Thr Phe Glu Asp Ser Thr Lys Lys Cys Ala Asp Ser
                    340                 345                 350

Asn Pro Arg Gly Val Ser Ala Tyr Leu Ser Arg Pro Ser Pro Phe Asp
                    355                 360                 365

Leu Phe Ile Arg Lys Ser Pro Thr Ile Thr Cys Leu Val Val Asp Leu
            370                 375                 380

Ala Pro Ser Lys Gly Thr Val Asn Leu Thr Trp Ser Arg Ala Ser Gly
385                 390                 395                 400

Lys Pro Val Asn His Ser Thr Arg Lys Glu Lys Gln Arg Asn Gly
                    405                 410                 415

Thr Leu Thr Val Thr Ser Thr Leu Pro Val Gly Thr Arg Asp Trp Ile
                    420                 425                 430

Glu Gly Glu Thr Tyr Gln Cys Arg Val Thr His Pro His Leu Pro Arg
            435                 440                 445

Ala Leu Met Arg Ser Thr Thr Lys Thr Ser Gly Pro Arg Ala Ala Pro
            450                 455                 460

Glu Val Tyr Ala Phe Ala Thr Pro Glu Trp Pro Gly Ser Arg Asp Lys
465                 470                 475                 480

Arg Thr Leu Ala Cys Leu Ile Gln Asn Phe Met Pro Glu Asp Ile Ser
                    485                 490                 495
```

```
Val Gln Trp Leu His Asn Glu Val Gln Leu Pro Asp Ala Arg His Ser
            500                 505                 510

Thr Thr Gln Pro Arg Lys Thr Lys Gly Ser Gly Phe Phe Val Phe Ser
            515                 520                 525

Arg Leu Glu Val Thr Arg Ala Glu Trp Glu Gln Lys Asp Glu Phe Ile
            530                 535                 540

Cys Arg Ala Val His Glu Ala Ala Ser Pro Ser Gln Thr Val Gln Arg
545                 550                 555                 560

Ala Val Ser Val Asn Pro Gly Lys
                565

<210> SEQ ID NO 30
<211> LENGTH: 593
<212> TYPE: PRT
<213> ORGANISM: Artificial Sequence
<220> FEATURE:
<223> OTHER INFORMATION: Synthetic

<400> SEQUENCE: 30

Met Leu Pro Cys Leu Val Val Leu Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
            35                  40                  45

Pro Asn Gln Ser Glu Ser Thr Cys Tyr Glu Val Ala Leu Leu Arg Tyr
            50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
            85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
            115                 120                 125

Ser Val Asn Leu Glu Ile His Asn Gly Phe Ile Leu Gly Lys Ile Gln
            130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
            165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Ile
            210                 215                 220

Ser Leu Thr Arg Gln Val Gln His Pro Asn Gly Asn Lys Glu Lys Asn
225                 230                 235                 240

Val Pro Leu Pro Val Ile Ala Glu Leu Pro Lys Val Ser Val Phe
            245                 250                 255

Val Pro Pro Arg Asp Gly Phe Phe Gly Asn Pro Arg Lys Ser Lys Leu
            260                 265                 270

Ile Cys Gln Ala Thr Gly Phe Ser Pro Arg Gln Ile Gln Val Ser Trp
            275                 280                 285
```

Leu Arg Glu Gly Lys Gln Val Gly Ser Gly Val Thr Asp Gln Val
            290                 295                 300

Gln Ala Glu Ala Lys Glu Ser Gly Pro Thr Thr Tyr Lys Val Thr Ser
305                 310                 315                 320

Thr Leu Thr Ile Lys Glu Ser Asp Trp Leu Ser Gln Ser Met Phe Thr
                325                 330                 335

Cys Arg Val Asp His Arg Gly Leu Thr Phe Gln Gln Asn Ala Ser Ser
                340                 345                 350

Met Cys Val Pro Asp Gln Asp Thr Ala Ile Arg Val Phe Ala Ile Pro
            355                 360                 365

Pro Ser Phe Ala Ser Ile Phe Leu Thr Lys Ser Thr Lys Leu Thr Cys
370                 375                 380

Leu Val Thr Asp Leu Thr Thr Tyr Asp Ser Val Thr Ile Ser Trp Thr
385                 390                 395                 400

Arg Gln Asn Gly Glu Ala Val Lys Thr His Thr Asn Ile Ser Glu Ser
                405                 410                 415

His Pro Asn Ala Thr Phe Ser Ala Val Gly Glu Ala Ser Ile Cys Glu
                420                 425                 430

Asp Asp Trp Asn Ser Gly Glu Arg Phe Thr Cys Thr Val Thr His Thr
            435                 440                 445

Asp Leu Pro Ser Pro Leu Lys Gln Thr Ile Ser Arg Pro Lys Gly Val
450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
            500                 505                 510

Ser Pro Glu Lys Tyr Val Thr Ser Ala Pro Met Pro Glu Pro Gln Ala
            515                 520                 525

Pro Gly Arg Tyr Phe Ala His Ser Ile Leu Thr Val Ser Glu Glu Glu
            530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
                580                 585                 590

Tyr

<210> SEQ ID NO 31
<211> LENGTH: 472
<212> TYPE: PRT
<213> ORGANISM: Artificial Sequence
<220> FEATURE:
<223> OTHER INFORMATION: Synthetic

<400> SEQUENCE: 31

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe His His Ile Leu His Trp Thr Pro Ile
        35                  40                  45

```
Pro Asn Gln Ser Glu Ser Thr Cys Tyr Glu Val Ala Leu Leu Arg Tyr
    50                  55                  60
Gly Ile Glu Ser Trp Asn Ser Ile Ser Asn Cys Ser Gln Thr Leu Ser
 65                  70                  75                  80
Tyr Asp Leu Thr Ala Val Thr Leu Asp Leu Tyr His Ser Asn Gly Tyr
                 85                  90                  95
Arg Ala Arg Val Arg Ala Val Asp Gly Ser Arg His Ser Asn Trp Thr
                100                 105                 110
Val Thr Asn Thr Arg Phe Ser Val Asp Glu Val Thr Leu Thr Val Gly
                115                 120                 125
Ser Val Asn Leu Glu Ile His Asn Gly Phe Ile Leu Gly Lys Ile Gln
130                 135                 140
Leu Pro Arg Pro Lys Met Ala Pro Ala Asn Asp Thr Tyr Glu Ser Ile
145                 150                 155                 160
Phe Ser His Phe Arg Glu Tyr Glu Ile Ala Ile Arg Lys Val Pro Gly
                165                 170                 175
Asn Phe Thr Phe Thr His Lys Lys Val Lys His Glu Asn Phe Ser Leu
                180                 185                 190
Leu Thr Ser Gly Glu Val Gly Glu Phe Cys Val Gln Val Lys Pro Ser
                195                 200                 205
Val Ala Ser Arg Ser Asn Lys Gly Met Trp Ser Lys Glu Glu Cys Ile
210                 215                 220
Ser Leu Thr Arg Gln Tyr Val Pro Lys Glu Phe Asn Ala Glu Thr Phe
225                 230                 235                 240
Thr Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
                275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
                340                 345                 350
Leu Pro Ala Pro Ile Glu Lys Thr Ile Ser Lys Ala Lys Gly Gln Pro
                355                 360                 365
Arg Glu Pro Gln Val Tyr Thr Leu Pro Pro Ser Arg Asp Glu Leu Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
                435                 440                 445
Ser Cys Ser Val Met His Glu Ala Leu His Asn His Tyr Thr Gln Lys
450                 455                 460
Ser Leu Ser Leu Ser Pro Gly Lys
```

465                  470

<210> SEQ ID NO 32
<211> LENGTH: 472
<212> TYPE: PRT
<213> ORGANISM: Artificial Sequence
<220> FEATURE:
<223> OTHER INFORMATION: Synthetic

<400> SEQUENCE: 32

```
Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Arg Glu Lys Gln Thr Asp Glu Ile Lys Asp Thr
225                 230                 235                 240

Arg Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
```

```
            355                 360                 365
Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys
465                 470

<210> SEQ ID NO 33
<211> LENGTH: 467
<212> TYPE: PRT
<213> ORGANISM: Artificial Sequence
<220> FEATURE:
<223> OTHER INFORMATION: Synthetic

<400> SEQUENCE: 33

Met Leu Ser Arg Leu Leu Pro Phe Leu Val Thr Ile Ser Ser Leu Ser
1               5                   10                  15

Leu Glu Phe Ile Ala Tyr Gly Thr Glu Leu Pro Ser Pro Ser Tyr Val
                20                  25                  30

Trp Phe Glu Ala Arg Phe Phe Gln His Ile Leu His Trp Lys Pro Ile
                35                  40                  45

Pro Asn Gln Ser Glu Ser Thr Tyr Tyr Glu Val Ala Leu Lys Gln Tyr
                50                  55                  60

Gly Asn Ser Thr Trp Asn Asp Ile His Ile Cys Arg Lys Ala Gln Ala
65                  70                  75                  80

Leu Ser Cys Asp Leu Thr Thr Phe Thr Leu Asp Leu Tyr His Arg Ser
                85                  90                  95

Tyr Gly Tyr Arg Ala Arg Val Arg Ala Val Asp Asn Ser Gln Tyr Ser
                100                 105                 110

Asn Trp Thr Thr Thr Glu Thr Arg Phe Thr Val Asp Glu Val Ile Leu
                115                 120                 125

Thr Val Asp Ser Val Thr Leu Lys Ala Met Asp Gly Ile Ile Tyr Gly
                130                 135                 140

Thr Ile His Pro Pro Arg Pro Thr Ile Thr Pro Ala Gly Asp Glu Tyr
145                 150                 155                 160

Glu Gln Val Phe Lys Asp Leu Arg Val Tyr Lys Ile Ser Ile Arg Lys
                165                 170                 175

Phe Ser Glu Leu Lys Asn Ala Thr Lys Arg Val Lys Gln Glu Thr Phe
                180                 185                 190

Thr Leu Thr Val Pro Ile Gly Val Arg Lys Phe Cys Val Lys Val Leu
                195                 200                 205

Pro Arg Leu Glu Ser Arg Ile Asn Lys Ala Glu Trp Ser Glu Glu Gln
                210                 215                 220

Cys Leu Leu Ile Thr Thr Glu Gln Ser Thr Lys Val Asp Lys Lys Ile
225                 230                 235                 240

Val Pro Arg Asp Cys Gly Cys Lys Pro Cys Ile Cys Thr Val Pro Glu
```

245                 250                 255
Val Ser Ser Val Phe Ile Phe Pro Pro Lys Pro Lys Asp Val Leu Thr
                260                 265                 270

Ile Thr Leu Thr Pro Lys Val Thr Cys Val Val Val Asp Ile Ser Lys
            275                 280                 285

Asp Asp Pro Glu Val Gln Phe Ser Trp Phe Val Asp Asp Val Glu Val
        290                 295                 300

His Thr Ala Gln Thr Gln Pro Arg Glu Glu Gln Phe Asn Ser Thr Phe
305                 310                 315                 320

Arg Ser Val Ser Glu Leu Pro Ile Met His Gln Asp Trp Leu Asn Gly
                325                 330                 335

Lys Glu Phe Lys Cys Arg Val Asn Ser Ala Ala Phe Pro Ala Pro Ile
            340                 345                 350

Glu Lys Thr Ile Ser Lys Thr Lys Gly Arg Pro Lys Ala Pro Gln Val
        355                 360                 365

Tyr Thr Ile Pro Pro Pro Lys Glu Gln Met Ala Lys Asp Lys Val Ser
    370                 375                 380

Leu Thr Cys Met Ile Thr Asp Phe Phe Pro Glu Asp Ile Thr Val Glu
385                 390                 395                 400

Trp Gln Trp Asn Gly Gln Pro Ala Glu Asn Tyr Lys Asn Thr Gln Pro
                405                 410                 415

Ile Met Asp Thr Asp Gly Ser Tyr Phe Val Tyr Ser Lys Leu Asn Val
            420                 425                 430

Gln Lys Ser Asn Trp Glu Ala Gly Asn Thr Phe Thr Cys Ser Val Leu
        435                 440                 445

His Glu Gly Leu His Asn His His Thr Glu Lys Ser Leu Ser His Ser
    450                 455                 460

Pro Gly Lys
465

<210> SEQ ID NO 34
<211> LENGTH: 232
<212> TYPE: PRT
<213> ORGANISM: Mus musculus

<400> SEQUENCE: 34

Met Leu Ser Arg Leu Leu Pro Phe Leu Val Thr Ile Ser Ser Leu Ser
1               5                   10                  15

Leu Glu Phe Ile Ala Tyr Gly Thr Glu Leu Pro Ser Pro Ser Tyr Val
            20                  25                  30

Trp Phe Glu Ala Arg Phe Phe Gln His Ile Leu His Trp Lys Pro Ile
        35                  40                  45

Pro Asn Gln Ser Glu Ser Thr Tyr Tyr Glu Val Ala Leu Lys Gln Tyr
    50                  55                  60

Gly Asn Ser Thr Trp Asn Asp Ile His Ile Cys Arg Lys Ala Gln Ala
65                  70                  75                  80

Leu Ser Cys Asp Leu Thr Thr Phe Thr Leu Asp Leu Tyr His Arg Ser
                85                  90                  95

Tyr Gly Tyr Arg Ala Arg Val Arg Ala Val Asp Asn Ser Gln Tyr Ser
            100                 105                 110

Asn Trp Thr Thr Thr Glu Thr Arg Phe Thr Val Asp Glu Val Ile Leu
        115                 120                 125

Thr Val Asp Ser Val Thr Leu Lys Ala Met Asp Gly Ile Ile Tyr Gly
    130                 135                 140

```
Thr Ile His Pro Pro Arg Pro Thr Ile Thr Pro Ala Gly Asp Glu Tyr
145                 150                 155                 160

Glu Gln Val Phe Lys Asp Leu Arg Val Tyr Lys Ile Ser Ile Arg Lys
                165                 170                 175

Phe Ser Glu Leu Lys Asn Ala Thr Lys Arg Val Lys Gln Glu Thr Phe
            180                 185                 190

Thr Leu Thr Val Pro Ile Gly Val Arg Lys Phe Cys Val Lys Val Leu
        195                 200                 205

Pro Arg Leu Glu Ser Arg Ile Asn Lys Ala Glu Trp Ser Glu Glu Gln
    210                 215                 220

Cys Leu Leu Ile Thr Thr Glu Gln
225                 230
```

<210> SEQ ID NO 35
<211> LENGTH: 12
<212> TYPE: PRT
<213> ORGANISM: Mus musculus

<400> SEQUENCE: 35

```
Ser Thr Lys Val Asp Lys Lys Ile Val Pro Arg Asp
1               5                   10
```

<210> SEQ ID NO 36
<211> LENGTH: 223
<212> TYPE: PRT
<213> ORGANISM: Mus musculus

<400> SEQUENCE: 36

```
Cys Gly Cys Lys Pro Cys Ile Cys Thr Val Pro Glu Val Ser Ser Val
1               5                   10                  15

Phe Ile Phe Pro Pro Lys Pro Lys Asp Val Leu Thr Ile Thr Leu Thr
                20                  25                  30

Pro Lys Val Thr Cys Val Val Val Asp Ile Ser Lys Asp Asp Pro Glu
            35                  40                  45

Val Gln Phe Ser Trp Phe Val Asp Asp Val Glu Val His Thr Ala Gln
50                  55                  60

Thr Gln Pro Arg Glu Glu Gln Phe Asn Ser Thr Phe Arg Ser Val Ser
65                  70                  75                  80

Glu Leu Pro Ile Met His Gln Asp Trp Leu Asn Gly Lys Glu Phe Lys
                85                  90                  95

Cys Arg Val Asn Ser Ala Ala Phe Pro Ala Pro Ile Glu Lys Thr Ile
            100                 105                 110

Ser Lys Thr Lys Gly Arg Pro Lys Ala Pro Gln Val Tyr Thr Ile Pro
        115                 120                 125

Pro Pro Lys Glu Gln Met Ala Lys Asp Lys Val Ser Leu Thr Cys Met
    130                 135                 140

Ile Thr Asp Phe Phe Pro Glu Asp Ile Thr Val Glu Trp Gln Trp Asn
145                 150                 155                 160

Gly Gln Pro Ala Glu Asn Tyr Lys Asn Thr Gln Pro Ile Met Asp Thr
                165                 170                 175

Asp Gly Ser Tyr Phe Val Tyr Ser Lys Leu Asn Val Gln Lys Ser Asn
            180                 185                 190

Trp Glu Ala Gly Asn Thr Phe Thr Cys Ser Val Leu His Glu Gly Leu
        195                 200                 205

His Asn His His Thr Glu Lys Ser Leu Ser His Ser Pro Gly Lys
    210                 215                 220
```

<210> SEQ ID NO 37
<211> LENGTH: 1419
<212> TYPE: DNA
<213> ORGANISM: Artificial Sequence
<220> FEATURE:
<223> OTHER INFORMATION: Synthetic

<400> SEQUENCE: 37

| | | | | | |
|---|---|---|---|---|---|
| atgctgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | attttccac | 120 |
| cacatcctcc | actggacacc | catcccaaat | cagtctgaaa | gtacctgcta | tgaagtggcg | 180 |
| ctcctgaggt | atggaataga | gtcctggaac | tccatctcca | actgtagcca | gaccctgtcc | 240 |
| tatgacctta | ccgcagtgac | cttggacctg | taccacagca | atggctaccg | ggccagagtg | 300 |
| cgggctgtgg | acggcagccg | gcactccaac | tggaccgtca | ccaacacccg | cttctctgtg | 360 |
| gatgaagtga | ctctgacagt | tggcagtgtg | aacctagaga | tccacaatgg | cttcatcctc | 420 |
| gggaagattc | agctacccag | gcccaagatg | gcccccgcaa | atgacacata | tgaaagcatc | 480 |
| ttcagtcact | tccgagagta | tgagattgcc | attcgcaagg | tgccgggaaa | cttcacgttc | 540 |
| acacacaaga | agtaaaaaca | tgaaaacttc | agcctcctaa | cctctggaga | agtgggagag | 600 |
| ttctgtgtcc | aggtgaaacc | atctgtcgct | tcccgaagta | caaggggat | gtggtctaaa | 660 |
| gaggagtgca | tctccctcac | caggcagaag | cccagcaaca | ccaaggtgga | caagagagtt | 720 |
| gagcccaaat | cttgtgacaa | aactcacaca | tgcccaccgt | gcccagcacc | tgaactcctg | 780 |
| gggggaccgt | cagtcttcct | cttccccca | aaacccaagg | acaccctcat | gatctcccgg | 840 |
| acccctgagg | tcacatgcgt | ggtggtggac | gtgagccacg | aagaccctga | ggtcaagttc | 900 |
| aactggtacg | tggacggcgt | ggaggtgcat | aatgccaaga | caaagccgcg | ggaggagcag | 960 |
| tacaacagca | cgtaccgtgt | ggtcagcgtc | ctcaccgtcc | tgcaccagga | ctggctgaat | 1020 |
| ggcaaggagt | acaagtgcaa | ggtctccaac | aaagccctcc | cagcccccat | cgagaaaacc | 1080 |
| atctccaaag | ccaaagggca | gccccgagaa | ccacaggtgt | acaccctgcc | cccatcccgg | 1140 |
| gatgagctga | ccaagaacca | ggtcagcctg | acctgcctgg | tcaaaggctt | ctatcccagc | 1200 |
| gacatcgccg | tggagtggga | gagcaatggg | cagccggaga | caactacaa | gaccacgcct | 1260 |
| cccgtgctgg | actccgacgg | ctccttcttc | ctctacagca | agctcaccgt | ggacaagagc | 1320 |
| aggtggcagc | aggggaacgt | cttctcatgc | tccgtgatgc | atgaggctct | gcacaaccac | 1380 |
| tacacgcaga | agagcctctc | cctgtctccg | ggtaaatga | | | 1419 |

<210> SEQ ID NO 38
<211> LENGTH: 1404
<212> TYPE: DNA
<213> ORGANISM: Artificial Sequence
<220> FEATURE:
<223> OTHER INFORMATION: Synthetic

<400> SEQUENCE: 38

| | | | | | |
|---|---|---|---|---|---|
| atgctgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | attttccac | 120 |
| cacatcctcc | actggacacc | catcccaaat | cagtctgaaa | gtacctgcta | tgaagtggcg | 180 |
| ctcctgaggt | atggaataga | gtcctggaac | tccatctcca | actgtagcca | gaccctgtcc | 240 |
| tatgacctta | ccgcagtgac | cttggacctg | taccacagca | atggctaccg | ggccagagtg | 300 |
| cgggctgtgg | acggcagccg | gcactccaac | tggaccgtca | ccaacacccg | cttctctgtg | 360 |

```
gatgaagtga ctctgacagt tggcagtgtg aacctagaga tccacaatgg cttcatcctc    420
gggaagattc agctacccag gcccaagatg gcccccgcaa atgacacata tgaaagcatc    480
ttcagtcact tccgagagta tgagattgcc attcgcaagg tgccgggaaa cttcacgttc    540
acacacaaga aagtaaaaca tgaaaacttc agcctcctaa cctctggaga agtgggagag    600
ttctgtgtcc aggtgaaacc atctgtcgct tcccgaagta acaaggggat gtggtctaaa    660
gaggagtgca tctccctcac caggcagaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960
ttccgtgtgg tcagcgtcct caccgttgtg caccaggact ggctgaacgg caaggagtac   1020
aagtgcaagg tctccaacaa aggcctccca gcccccatcg agaaaaccat ctccaaaacc   1080
aaagggcagc cccgagaacc acaggtgtac accctgcccc catcccggga ggagatgacc   1140
aagaaccagg tcagcctgac ctgcctggtc aaaggcttct accccagcga catctccgtg   1200
gagtgggaga gcaatgggca gccggagaac aactacaaga ccacacctcc catgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaa                                          1404
```

<210> SEQ ID NO 39
<211> LENGTH: 1557
<212> TYPE: DNA
<213> ORGANISM: Artificial Sequence
<220> FEATURE:
<223> OTHER INFORMATION: Synthetic

<400> SEQUENCE: 39

```
atgctgccgt gcctcgtagt gctgctggcg gcgctcctca gcctccgtct tggctcagac     60
gctcatggga cagagctgcc cagccctccg tctgtgtggt ttgaagcaga atttttccac    120
cacatcctcc actggacacc catcccaaat cagtctgaaa gtacctgcta tgaagtggcg    180
ctcctgaggt atgaaataga gtcctggaac tccatctcca actgtagcca gaccctgtcc    240
tatgacctta ccgcagtgac cttggacctg taccacagca atggctaccg ggccagagtg    300
cgggctgtga cgcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg gcccccgcaa atgacacata tgaaagcatc    480
ttcagtcact tccgagagta tgagattgcc attcgcaagg tgccgggaaa cttcacgttc    540
acacacaaga aagtaaaaca tgaaaacttc agcctcctaa cctctggaga agtgggagag    600
ttctgtgtcc aggtgaaacc atctgtcgct tcccgaagta acaaggggat gtggtctaaa    660
gaggagtgca tctccctcac caggcagaag cccagcaaca ccaaggtgga caagagagtt    720
gagctcaaaa ccccacttgg tgacacaact cacacatgcc cacggtgccc agagcccaaa    780
tcttgtgaca cacctccccc gtgcccacgg tgcccagagc ccaaatcttg tgacacacct    840
cccccatgcc cacggtgccc agagcccaaa tcttgtgaca cacctccccc gtgcccaagg    900
tgcccagcac ctgaactcct gggaggaccg tcagtcttcc tcttcccccc aaaacccaag    960
```

```
gataccctta tgatttcccg gaccectgag gtcacgtgcg tggtggtgga cgtgagccac    1020
gaagaccccg aggtccagtt caagtggtac gtggacggcg tggaggtgca taatgccaag    1080
acaaagccgc gggaggagca gtacaacagc acgttccgtg tggtcagcgt cctcaccgtc    1140
ctgcaccagg actggctgaa cggcaaggag tacaagtgca aggtctccaa caaagccctc    1200
ccagccccca tcgagaaaac catctccaaa accaaggac agccccgaga ccacaggtg     1260 tacaccctgc ccccatcccg ggaggagatg accaagaacc aggtcagcct gacctgcctg    1320
gtcaaaggct tctaccccag cgacatcgcc gtggagtggg agagcagcgg gcagccggag    1380
aacaactaca acaccacgcc tcccatgctg gactccgacg gctccttctt cctctacagc    1440
aagctcaccg tggacaagag caggtggcag caggggaaca tcttctcatg ctccgtgatg    1500
catgaggctc tgcacaaccg cttcacgcag aagagcctct ccctgtctcc gggtaaa      1557
```

<210> SEQ ID NO 40
<211> LENGTH: 1407
<212> TYPE: DNA
<213> ORGANISM: Artificial Sequence
<220> FEATURE:
<223> OTHER INFORMATION: Synthetic

<400> SEQUENCE: 40

```
atgctgccgt gcctcgtagt gctgctggcg gcgctcctca gcctccgtct tggctcagac     60
gctcatggga cagagctgcc cagccctccg tctgtgtggt ttgaagcaga attttccac    120 cacatcctcc actggacacc catcccaaat cagtctgaaa gtacctgcta tgaagtggcg    180
ctcctgaggt atgaaataga gtcctggaac tccatctcca actgtagcca gaccctgtcc    240
tatgacctta ccgcagtgac cttggacctg taccacagca atggctaccg gccagagtg    300 cgggctgtgg acgcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg gcccccgcaa atgacacata tgaaagcatc    480
ttcagtcact tccgagagta tgagattgcc attcgcaagg tgccgggaaa cttcacgttc    540
acacacaaga agtaaaaaca tgaaaacttc agcctcctaa cctctggaga agtgggagag    600
ttctgtgtcc aggtgaaacc atctgtcgct tcccgaagta caagggggat gtggtctaaa    660
gaggagtgca ctccctcac caggcagaag cccagcaaca ccaaggtgga caagagagtt    720
gagtccaaat atggtccccc atgcccatca tgcccagcac ctgagttcct gggggggacca    780 tcagtcttcc tgttcccccc aaaacccaag gacactctca tgatctcccg gaccctgag     840 gtcacgtgcg tggtggtgga cgtgagccag gaagaccccg aggtccagtt caactggtac    900
gtggatggcg tggaggtgca taatgccaag acaaagccgc gggaggagca gttcaacagc    960
acgtaccgtg tggtcagcgt cctcaccgtc ctgcaccagg actggctgaa cggcaaggag    1020
tacaagtgca aggtctccaa caaaggcctc ccgtcctcca tcgagaaaac catctccaaa    1080
gccaaagggc agccccgaga gccacaggtg tacaccctgc ccccatccca ggaggagatg    1140
accaagaacc aggtcagcct gacctgcctg gtcaaaggct tctaccccag cgacatcgcc    1200
gtggagtggg agagcaatgg gcagccggag aacaactaca agaccacgcc tcccgtgctg    1260
gactccgacg gctccttctt cctctacagc aggctaaccg tggacaagag caggtggcag    1320 gagggggaatg tcttctcatg ctccgtgatg catgaggctc tgcacaacca ctacacacag    1380
aagagcctct ccctgtctct gggtaaa                                        1407
```

<210> SEQ ID NO 41
<211> LENGTH: 1488
<212> TYPE: DNA
<213> ORGANISM: Artificial Sequence
<220> FEATURE:
<223> OTHER INFORMATION: Synthetic

<400> SEQUENCE: 41

| | | | | | |
|---|---|---|---|---|---|
| atgctgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | atttttccac | 120 |
| cacatcctcc | actggacacc | catcccaaat | cagtctgaaa | gtacctgcta | tgaagtggcg | 180 |
| ctcctgaggt | atggaataga | gtcctggaac | tccatctcca | actgtagcca | gaccctgtcc | 240 |
| tatgacctta | ccgcagtgac | cttggacctg | taccacagca | atggctaccg | ggccagagtg | 300 |
| cgggctgtgg | acggcagccg | gcactccaac | tggaccgtca | ccaacacccg | cttctctgtg | 360 |
| gatgaagtga | ctctgacagt | tggcagtgtg | aacctagaga | tccacaatgg | cttcatcctc | 420 |
| gggaagattc | agctacccag | gcccaagatg | gcccccgcaa | atgacacata | tgaaagcatc | 480 |
| ttcagtcact | tccgagagta | tgagattgcc | attcgcaagg | tgccgggaaa | cttcacgttc | 540 |
| acacacaaga | agtaaaaaca | tgaaaacttc | agcctcctaa | cctctggaga | agtgggagag | 600 |
| ttctgtgtcc | aggtgaaacc | atctgtcgct | tcccgaagta | caaggggat | gtggtctaaa | 660 |
| gaggagtgca | tctccctcac | caggcaggtg | aagcactaca | cgaatcccag | ccaggatgtg | 720 |
| actgtgccct | gcccagttcc | ctcaactcca | cctaccccat | ctccctcaac | tccacctacc | 780 |
| ccatctccct | catgctgcca | cccccgactg | tcactgcacc | gaccggccct | cgaggacctg | 840 |
| ctcttaggtt | cagaagcgaa | cctcacgtgc | acactgaccg | gctgagaga | tgcctcaggt | 900 |
| gtcaccttca | cctggacgcc | ctcaagtggg | aagagcgctg | ttcaaggacc | acctgagcgt | 960 |
| gacctctgtg | gctgctacag | cgtgtccagt | gtcctgccgg | gctgtgccga | gccatggaac | 1020 |
| catgggaaga | ccttcacttg | cactgctgcc | taccccgagt | ccaagacccc | gctaaccgcc | 1080 |
| accctctcaa | aatccggaaa | cacattccgg | cccgaggtcc | acctgctgcc | gccgccgtcg | 1140 |
| gaggagctgg | ccctgaacga | gctggtgacg | ctgacgtgcc | tggcacgtgg | cttcagcccc | 1200 |
| aaggatgtgc | tggttcgctg | gctgcagggg | tcacaggagc | tgccccgcga | agtacctg | 1260 |
| acttgggcat | cccggcagga | gcccagccag | ggcaccacca | ccttcgctgt | gaccagcata | 1320 |
| ctgcgcgtgg | cagccgagga | ctggaagaag | ggggacacct | tctcctgcat | ggtgggccac | 1380 |
| gaggccctgc | cgctggcctt | cacacagaag | accatcgacc | gcttggcggg | taaacccacc | 1440 |
| catgtcaatg | tgtctgttgt | catggcggag | gtggacggca | cctgctac | | 1488 |

<210> SEQ ID NO 42
<211> LENGTH: 1449
<212> TYPE: DNA
<213> ORGANISM: Artificial Sequence
<220> FEATURE:
<223> OTHER INFORMATION: Synthetic

<400> SEQUENCE: 42

| | | | | | |
|---|---|---|---|---|---|
| atgctgccgt | gcctcgtagt | gctgctggcg | gcgctcctca | gcctccgtct | tggctcagac | 60 |
| gctcatggga | cagagctgcc | cagccctccg | tctgtgtggt | ttgaagcaga | atttttccac | 120 |
| cacatcctcc | actggacacc | catcccaaat | cagtctgaaa | gtacctgcta | tgaagtggcg | 180 |
| ctcctgaggt | atggaataga | gtcctggaac | tccatctcca | actgtagcca | gaccctgtcc | 240 |
| tatgacctta | ccgcagtgac | cttggacctg | taccacagca | atggctaccg | ggccagagtg | 300 |

| | |
|---|---|
| cgggctgtgg acggcagccg gcactccaac tggaccgtca ccaacacccg cttctctgtg | 360 |
| gatgaagtga ctctgacagt tggcagtgtg aacctagaga tccacaatgg cttcatcctc | 420 |
| gggaagattc agctacccag gcccaagatg gcccccgcaa atgacacata tgaaagcatc | 480 |
| ttcagtcact tccgagagta tgagattgcc attcgcaagg tgccgggaaa cttcacgttc | 540 |
| acacacaaga agtaaaaaca tgaaaacttc agcctcctaa cctctggaga agtgggagag | 600 |
| ttctgtgtcc aggtgaaacc atctgtcgct tcccgaagta acaaggggat gtggtctaaa | 660 |
| gaggagtgca tctccctcac caggcaggtg aagcactaca cgaatcccag ccaggatgtg | 720 |
| actgtgccct gcccagttcc cccacctccc ccatgctgcc accccgact gtcgctgcac | 780 |
| cgaccggccc tcgaggacct gctcttaggt tcagaagcga acctcacgtg cacactgacc | 840 |
| ggcctgagag atgcctctgg tgccaccttc acctggacgc cctcaagtgg gaagagcgct | 900 |
| gttcaaggac cacctgagcg tgacctctgt ggctgctaca gcgtgtccag tgtcctgcct | 960 |
| ggctgtgccc agccatggaa ccatggggag accttcacct gcactgctgc caccccgag | 1020 |
| ttgaagaccc cactaaccgc caacatcaca aaatccggaa acacattccg gcccgaggtc | 1080 |
| cacctgctgc cgccgccgtc ggaggagctg gccctgaacg agctggtgac gctgacgtgc | 1140 |
| ctggcacgtg gcttcagccc caaggatgtg ctggttcgct ggctgcaggg gtcacaggag | 1200 |
| ctgccccgcg agaagtacct gacttgggca tcccggcagg agcccagcca gggcaccacc | 1260 |
| accttcgctg tgaccagcat actgcgcgtg gcagccgagg actggaagaa gggggacacc | 1320 |
| ttctcctgca tggtgggcca cgaggccctg ccgctggcct tcacacagaa gaccatcgac | 1380 |
| cgcatggcgg gtaaacccac ccatgtcaat gtgtctgttg tcatggcgga ggtggacggc | 1440 |
| acctgctac | 1449 |

<210> SEQ ID NO 43
<211> LENGTH: 1575
<212> TYPE: DNA
<213> ORGANISM: Artificial Sequence
<220> FEATURE:
<223> OTHER INFORMATION: Synthetic

<400> SEQUENCE: 43

| | |
|---|---|
| atgctgccgt gcctcgtagt gctgctggcg gcgctcctca gcctccgtct tggctcagac | 60 |
| gctcatggga cagagctgcc cagccctccg tctgtgtggt ttgaagcaga attttttccac | 120 |
| cacatcctcc actggacacc catcccaaat cagtctgaaa gtacctgcta tgaagtggcg | 180 |
| ctcctgaggt atggaataga gtcctggaac tccatctcca actgtagcca gaccctgtcc | 240 |
| tatgacctta ccgcagtgac cttggacctg taccacagca tggctaccg ggccagagtg | 300 |
| cgggctgtgg acggcagccg gcactccaac tggaccgtca ccaacacccg cttctctgtg | 360 |
| gatgaagtga ctctgacagt tggcagtgtg aacctagaga tccacaatgg cttcatcctc | 420 |
| gggaagattc agctacccag gcccaagatg gcccccgcaa atgacacata tgaaagcatc | 480 |
| ttcagtcact tccgagagta tgagattgcc attcgcaagg tgccgggaaa cttcacgttc | 540 |
| acacacaaga agtaaaaaca tgaaaacttc agcctcctaa cctctggaga agtgggagag | 600 |
| ttctgtgtcc aggtgaaacc atctgtcgct tcccgaagta acaaggggat gtggtctaaa | 660 |
| gaggagtgca tctccctcac caggcagacc gccagcaaga gtaagaagga gatcttccgc | 720 |
| tggccagagt ctccaaaggc acaggcctcc tcagtgccca ctgcacaacc ccaagcagag | 780 |
| ggcagcctcg ccaaggcaac cacagcccca gccaccaccc gtaacacagg aagaggagga | 840 |
| gaagagaaga agaaggagaa ggagaaagag gaacaagaag agagagagac aaagacacca | 900 |

```
gagtgtccga gccacaccca gcctcttggc gtctacctgc taacccctgc agtgcaggac    960
ctgtggctcc gggacaaagc caccttcacc tgcttcgtgg tgggcagtga cctgaaggat   1020
gctcacctga cctgggaggt ggccgggaag gtccccacag ggggcgtgga ggaagggctg   1080
ctggagcggc acagcaacgg ctcccagagc cagcacagcc gtctgaccct gcccaggtcc   1140
ttgtggaacg cggggacctc cgtcacctgc acactgaacc atcccagcct cccaccccag   1200
aggttgatgg cgctgagaga acccgctgcg caggcacccg tcaagctttc cctgaacctg   1260
ctggcctcgt ctgaccctcc cgaggcggcc tcgtggctcc tgtgtgaggt gtctggcttc   1320 tcgccccca acatcctcct gatgtggctg aggaccagc gtgaggtgaa cacttctggg    1380 tttgccccg cacgccccc tccacagccc gggagcacca cgttctgggc ctggagtgtg    1440
ctgcgtgtcc cagccccgcc cagccctcag ccagccacct acacgtgtgt ggtcagccac   1500
gaggactccc ggactctgct caacgccagc cggagcctag aagtcagcta tgtaacagac   1560
catggcccca tgaaa                                                    1575

<210> SEQ ID NO 44
<211> LENGTH: 1704
<212> TYPE: DNA
<213> ORGANISM: Artificial Sequence
<220> FEATURE:
<223> OTHER INFORMATION: Synthetic

<400> SEQUENCE: 44
atgctgccgt gcctcgtagt gctgctggcg gcgctcctca gcctccgtct tggctcagac     60
gctcatggga cagagctgcc cagccctccg tctgtgtggt ttgaagcaga atttttccac    120
cacatcctcc actggacacc catcccaaat cagtctgaaa gtacctgcta tgaagtggcg    180
ctcctgaggt atggaataga gtcctggaac tccatctcca actgtagcca gaccctgtcc    240
tatgacctta ccgcagtgac cttggacctg taccacagca atggctaccg ggccagagtg    300
cgggctgtgg acggcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg gccccccgcaa atgacacata tgaaagcatc    480
ttcagtcact tccgagagta tgagattgcc attcgcaagg tgccgggaaa cttcacgttc    540
acacacaaga agtaaaaca tgaaaacttc agcctcctaa cctctggaga agtgggagag    600
ttctgtgtcc aggtgaaacc atctgtcgct tcccgaagta caagggat gtggtctaaa    660 gaggagtgca tctcctcac caggcagact ccatcgtcca cagactggt cgacaacaaa    720 accttcagcg tctgctccag ggacttcacc ccgcccaccg tgaagatctt acagtcgtcc    780
tgcgacggcg gcgggcactt cccccgacc atccagctcc tgtgcctcgt ctctgggtac    840
accccaggga ctatcaacat cacctggctg gaggacgggc aggtcatgga cgtggacttg    900
tccaccgcct ctaccacgca ggagggtgag ctggcctcca caaaagcga gctcacccc    960 agccagaagc actggctgtc agaccgcacc tacacctgcc aggtcaccta tcaaggtcac   1020
acctttgagg acagcaccaa gaagtgtgca gattccaacc cgagagggt gagcgcctac   1080 ctaagccggc ccagcccgtt cgacctgttc atccgcaagt cgcccacgat cacctgtctg   1140
gtggtggacc tggcacccag caaggggacc gtgaacctga cctggtcccg ggccagtggg   1200
aagcctgtga accactccac cagaaaggag gagaagcagc gcaatggcac gttaaccgtc   1260
acgtccaccc tgccggtggg cacccgagac tggatcgagg gggagaccta ccagtgcagg   1320
```

-continued

| | |
|---|---|
| gtgacccacc cccacctgcc cagggccctc atgcggtcca cgaccaagac cagcggcccg | 1380 |
| cgtgctgccc cggaagtcta tgcgtttgcg acgccggagt ggccggggag ccgggacaag | 1440 |
| cgcaccctcg cctgcctgat ccagaacttc atgcctgagg acatctcggt gcagtggctg | 1500 |
| cacaacgagg tgcagctccc ggacgccgg cacagcacga cgcagccccg caagaccaag | 1560 |
| ggctccggct tcttcgtctt cagccgcctg gaggtgacca gggccgaatg ggagcagaaa | 1620 |
| gatgagttca tctgccgtgc agtccatgag gcagcgagcc cctcacagac cgtccagcga | 1680 |
| gcggtgtctg taaatcccgg taaa | 1704 |

<210> SEQ ID NO 45
<211> LENGTH: 1779
<212> TYPE: DNA
<213> ORGANISM: Artificial Sequence
<220> FEATURE:
<223> OTHER INFORMATION: Synthetic

<400> SEQUENCE: 45

| | |
|---|---|
| atgctgccgt gcctcgtagt gctgctggcg gcgctcctca gcctccgtct tggctcagac | 60 |
| gctcatggga cagagctgcc cagccctccg tctgtgtggt ttgaagcaga atttttccac | 120 |
| cacatcctcc actggacacc catcccaaat cagtctgaaa gtacctgcta tgaagtggcg | 180 |
| ctcctgaggt atggaataga gtcctggaac tccatctcca actgtagcca gaccctgtcc | 240 |
| tatgacctta ccgcagtgac cttggacctg taccacagca atggctaccg ggccagagtg | 300 |
| cgggctgtgg acggcagccg gcactccaac tggaccgtca ccaacacccg cttctctgtg | 360 |
| gatgaagtga ctctgacagt tggcagtgtg aacctagaga tccacaatgg cttcatcctc | 420 |
| gggaagattc agctacccag gcccaagatg gccccgcaa atgacacata tgaaagcatc | 480 |
| ttcagtcact ccgagagta tgagattgcc attcgcaagg tgccgggaaa cttcacgttc | 540 |
| acacacaaga agtaaaaaca tgaaaacttc agcctcctaa cctctggaga agtgggagag | 600 |
| ttctgtgtcc aggtgaaacc atctgtcgct tcccgaagta acaagggat gtggtctaaa | 660 |
| gaggagtgca tctcccctcac caggcaggtc cagcacccca acggcaacaa agaaaagaac | 720 |
| gtgcctcttc cagtgattgc tgagctgcct cccaaagtga cgtcttcgt cccacccgc | 780 |
| gacggcttct tcggcaaccc ccgcaagtcc aagctcatct gccaggccac gggtttcagt | 840 |
| ccccggcaga ttcaggtgtc ctggctgcgc gaggggaagc aggtggggtc tggcgtcacc | 900 |
| acggaccagg tgcaggctga ggccaaagag tctgggccca cgacctacaa ggtgaccagc | 960 |
| acactgacca tcaaagagag cgactggctc agccagagca tgttcacctg ccgcgtggat | 1020 |
| cacaggggcc tgaccttcca gcagaatgcg tcctccatgt gtgtcccga tcaagacaca | 1080 |
| gccatccggg tcttcgccat ccccccatcc tttgccagca tcttcctcac caagtccacc | 1140 |
| aagttgacct gcctggtcac agacctgacc acctatgaca gcgtgaccat ctcctggacc | 1200 |
| cgccagaatg gcgaagctgt gaaaacccac accaacatct ccgagagcca ccccaatgcc | 1260 |
| actttcagcg ccgtgggtga ggccagcatc tgcgaggatg actggaattc cggggagagg | 1320 |
| ttcacgtgca ccgtgaccca cacagacctg ccctcgccac tgaagcagac catctcccgg | 1380 |
| cccaagggg tggccctgca caggcccgat gtctacttgc tgccaccagc ccgggagcag | 1440 |
| ctgaacctgc gggagtcggc caccatcacg tgcctggtga cgggcttctc tccgcggac | 1500 |
| gtcttcgtgc agtggatgca gagggggcag ccctgtccc ggagaagta tgtgaccagc | 1560 |
| gccccaatgc ctgagcccca ggccccaggc cggtacttcg cccacagcat cctgaccgtg | 1620 |
| tccgaagagg aatggaacac ggggagacc tacacctgcg tggtggccca tgaggccctg | 1680 | cccaacaggg tcaccgagag gaccgtggac aagtccaccg gtaaacccac cctgtacaac     1740 gtgtccctgg tcatgtccga cacagctggc acctgctac                            1779

<210> SEQ ID NO 46
<211> LENGTH: 1416
<212> TYPE: DNA
<213> ORGANISM: Artificial Sequence
<220> FEATURE:
<223> OTHER INFORMATION: Synthetic

<400> SEQUENCE: 46
atgctgccgt gcctcgtagt gctgctggcg gcgctcctca gcctccgtct tggctcagac       60
gctcatggga cagagctgcc cagccctccg tctgtgtggt ttgaagcaga attttttccac     120 cacatcctcc actggacacc catcccaaat cagtctgaaa gtacctgcta tgaagtggcg     180
ctcctgaggt atggaataga gtcctggaac tccatctcca actgtagcca gaccctgtcc     240
tatgacctta ccgcagtgac cttggacctg taccacagca atggctaccg ggccagagtg     300
cgggctgtgg acggcagccg gcactccaac tggaccgtca ccaacacccg cttctctgtg     360
gatgaagtga ctctgacagt tggcagtgtg aacctagaga tccacaatgg cttcatcctc     420
gggaagattc agctacccag gcccaagatg gcccccgcaa atgacacata tgaaagcatc     480
ttcagtcact tccgagagta tgagattgcc attcgcaagg tgccgggaaa cttcacgttc     540
acacacaaga aagtaaaaca tgaaaacttc agcctcctaa cctctggaga agtgggagag     600
ttctgtgtcc aggtgaaacc atctgtcgct tcccgaagta acaaggggat gtggtctaaa     660
gaggagtgca tctccctcac caggcagtac gttcccaaag agtttaatgc tgaaacattc     720 accccccaaat cttgtgacaa aactcacaca tgcccaccgt gcccagcacc tgaactcctg     780
gggggaccgt cagtcttcct cttccccccca aaacccaagg acaccctcat gatctcccgg     840 accccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtctccaac aaagcccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct    1260 cccgtgctga ctccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaa                              1416

<210> SEQ ID NO 47
<211> LENGTH: 1416
<212> TYPE: DNA
<213> ORGANISM: Artificial Sequence
<220> FEATURE:
<223> OTHER INFORMATION: Synthetic

<400> SEQUENCE: 47
atgctgccgt gcctcgtagt gctgctggcg gcgctcctca gcctccgtct tggctcagac       60
gctcatggga cagagctgcc cagccctccg tctgtgtggt ttgaagcaga attttttccac     120 cacatcctcc actggacacc catcccaaat cagtctgaaa gtacctgcta tgaagtggcg     180

```
ctcctgaggt atggaataga gtcctggaac tccatctcca actgtagcca gaccctgtcc    240
tatgacctta ccgcagtgac cttggacctg taccacagca atggctaccg ggccagagtg    300
cgggctgtgg acggcagccg gcactccaac tggaccgtca ccaacacccg cttctctgtg    360
gatgaagtga ctctgacagt tggcagtgtg aacctagaga tccacaatgg cttcatcctc    420
gggaagattc agctacccag gcccaagatg gcccccgcaa atgacacata tgaaagcatc    480
ttcagtcact tccgagagta tgagattgcc attcgcaagg tgccgggaaa cttcacgttc    540
acacacaaga agtaaaaaca tgaaaacttc agcctcctaa cctctggaga agtgggagag    600
ttctgtgtcc aggtgaaacc atctgtcgct tcccgaagta acaaggggat gtggtctaaa    660
gaggagtgca tctccctcac caggcagaga gaaaaacaga ctgatgaaat caaggatact    720
aggcccaaat cttgtgacaa aactcacaca tgcccaccgt gcccagcacc tgaactcctg    780
gggggaccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagcccctc cagcccccat cgagaaaacc   1080
atctccaaag ccaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga caactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416
```

<210> SEQ ID NO 48
<211> LENGTH: 462
<212> TYPE: PRT
<213> ORGANISM: Artificial Sequence
<220> FEATURE:
<223> OTHER INFORMATION: Synthetic

<400> SEQUENCE: 48

```
Met Leu Pro Cys Leu Val Val Leu Ala Ala Leu Leu Ser Leu Arg
1               5                   10                  15

Leu Gly Ser Asp Ala His Gly Thr Glu Leu Pro Ser Pro Ser Val
                20                  25                  30

Trp Phe Glu Ala Glu Phe Phe His Ile Leu His Trp Thr Pro Ile
            35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140
```

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
            165                 170                 175

Asn Phe Thr Phe Thr His Lys Lys Val Lys His Glu Asn Phe Ser Leu
        180                 185                 190

Leu Thr Ser Gly Glu Val Gly Glu Phe Cys Val Gln Val Lys Pro Ser
    195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
450                 455                 460

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 4
<212> TYPE: PRT
<213> ORGANISM: Artificial Sequence
<220> FEATURE:

```
<223> OTHER INFORMATION: Furin cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be Lys or Arg

<400> SEQUENCE: 50

Arg Xaa Xaa Arg
1

```
cgcccgacat cacctgtgtc tagagaatgc aatagtagta cggatagctg tgactccggt    1380
ccttctaaca cacctcctga gatacacccg gtggtcccgc tgtgcccat taaaccagtt    1440 gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatgggcgg ggcttaaagg gtatataatg    1680
cgccgtgggc taatcttggt tacatctgac ctcatggagg cttgggagtg tttggaagat    1740 tttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgctttttt gagttttata aaggataaat ggagcgaaga aacccatctg    2040 agcgggggt acctgctgga ttttctggcc atgcatctgt ggagagcggt tgtgagacac    2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaact tgtaaatatc aggaattgtt gctacatttc tgggaacggg gccgaggtgg    2640
agatagatac ggaggatagg gtggccttta gatgtagcat gataaatatg tggccggggg    2700
tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgt ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggcagtg tttgagcata    3180 acatactgac ccgctgttcc ttgcatttgg gtaacaggag gggggtgttc ctaccttacc    3240
aatgcaattt gagtcacact aagatattgc ttgagcccga gcatgtgcc aaggtgaacc    3300 tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
```

```
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aacataaat aaaaaaccag actctgtttg gatttggatc aagcaagtgt     4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320
ctttcagtag caagctgatt gccagggca ggcccttggt gtaagtgttt acaaagcgt      4380
taagctggga tgggtgcata cgtggggata tgagatgcat cttggactgt attttaggt     4440
tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccattttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgttt    5040
ccctgaccaa atccgccaga aggcgctcgc cgcccagcga tagcagttct gcaaggaag    5100
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacgggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca acttttgag ggcgtagagc ttgggcgcga gaaataccga    5580
ttccggggga taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa ggggggctat aaaagggggt ggggcgcgt tcgtcctcac tctcttccgc    6060
```

```
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtaggggtc    6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atgggtggg tgagcgcgga    6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtcccttt ttttccacag ctcgcggttg aggacaaact cttcgcggtc    7140
tttccagtac tcttggatcg gaaacccgtc ggcctccgaa cggtaagagc ctagcatgta   7200
gaactggttg acggcctggt aggcgcagca tcccttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgcttttg gaacgcggat ttggcagggc gaaggtgaca tcgttgaaga gtatctttcc    7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat ttttaagtt cctcgtaggt    7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca agtccagatt gtccgcgcgc ggcggtcgga gcttgatgac   8340
aacatcgcgc agatgggagc tgtccatggt ctggagctcc cgcggcgtca ggtcaggcgg   8400
```

```
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640
agaggggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacgcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcggccc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccggggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataaggccc tccccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacgcgc ggccgttctc gcgggggcgc   9540
agttggaaga cgccgcccgt catgtcccgg ttatgggttg gcgggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgtttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
```

```
gctgctgcgc tagcttttt  ggccactggc cgcgcgcagc gtaagcggtt aggctggaaa   10860
gcgaaagcat taagtggctc gctccctgta gccggagggt tattttccaa gggttgagtc   10920
gcgggacccc cggttcgagt ctcggaccgg ccggactgcg gcgaacgggg gtttgcctcc   10980
ccgtcatgca agacccgct  tgcaaattcc tccggaaaca gggacgagcc ccttttttgc   11040
ttttcccaga tgcatccggt gctgcggcag atgcgccccc ctcctcagca gcggcaagag   11100
caagagcagc ggcagacatg cagggcaccc tccctcctc  ctaccgcgtc aggagggggcg  11160
acatccgcgg ttgacgcggc agcagatggt gattacgaac ccccgcggcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaagctt  taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940
gagggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt gggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
```

```
tccaggagat tacaagtgtc agccgcgcgc tggggcagga ggacacgggc agcctggagg   13200
caaccctaaa ctacctgctg accaaccggc ggcagaagat ccctcgttg cacagtttaa    13260 acagcgagga ggagcgcatt ttgcgctacg tgcagcagag cgtgagcctt aacctgatgc   13320 gcgacgggt aacgcccagc gtggcgctgg acatgaccgc gcgcaacatg gaacgggca    13380 tgtatgcctc aaaccggccg tttatcaacc gcctaatgga ctacttgcat cgcgcggccg   13440
ccgtgaaccc cgagtatttc accaatgcca tcttgaaccc gcactggcta ccgcccctg    13500 gtttctacac cgggggattc gaggtgcccg agggtaacga tggattcctc tgggacgaca   13560
tagacgacag cgtgtttttcc ccgcaaccgc agaccctgct agagttgcaa cagcgcgagc  13620
aggcagaggc ggcgctgcga aaggaaagct tccgcaggcc aagcagcttg tccgatctag   13680
gcgctgcggc cccgcggtca gatgctagta gcccatttcc aagcttgata gggtctctta   13740
ccagcactcg caccacccgc ccgcgcctgc tgggcgagga ggagtaccta aacaactcgc   13800
tgctgcagcc gcagcgcgaa aaaaacctgc ctccggcatt tcccaacaac gggatagaga   13860
gcctagtgga caagatgagt agatggaaga cgtacgcgca ggagcacagg gacgtgccag   13920
gcccgcgccc gcccacccgt cgtcaaaggc acgaccgtca gcggggtctg gtgtgggagg   13980
acgatgactc ggcagacgac agcagcgtcc tggatttggg agggagtggc aacccgtttg   14040
cgcaccttcg ccccaggctg gggagaatgt tttaaaaaaa aaaaagcatg atgcaaaata   14100
aaaaactcac caaggccatg gcaccgagcg ttggttttct tgtattcccc ttagtatgcg   14160
gcgcgcggcg atgtatgagg aaggtcctcc tccctcctac gagagtgtgg tgagcgcggc   14220
gccagtggcg gcgcgctgg gttctccctt cgatgctccc ctggaccgc cgtttgtgcc    14280 tccgcggtac ctgcggccta ccgggggag aaacagcatc cgttactctg agttggcacc    14340
cctattcgac accacccgtg tgtacctggt ggacaacaag tcaacggatg tggcatccct   14400
gaactaccag aacgaccaca gcaactttct gaccacggtc attcaaaaca atgactacag   14460
cccgggggag gcaagcacac agaccatcaa tcttgacgac cggtcgcact ggggcggcga   14520
cctgaaaacc atcctgcata ccaacatgcc aaatgtgaac gagttcatgt ttaccaataa   14580
gtttaaggcg cgggtgatgg tgtcgcgctt gcctactaag gacaatcagg tggagctgaa   14640
atacgagtgg gtggagttca cgctgcccga gggcaactac tccgagacca tgaccataga   14700
ccttatgaac aacgcgatcg tggagcacta cttgaaagtg ggcagacaga acggggttct   14760
ggaaagcgac atcggggtaa agtttgacac ccgcaacttc agactggggt ttgaccccgt   14820
cactggtctt gtcatgcctg ggtatatac aaacgaagcc ttccatccag acatcatttt    14880
gctgccagga tgcggggtgg acttcaccca cagccgcctg agcaacttgt tgggcatccg   14940
caagcggcaa cccttccagg agggctttag gatcacctac gatgatcggg agggtggtaa   15000 cattccccgca ctgttggatg tggacgccta ccaggcgagc ttgaaagatg acaccgaaca   15060 gggcggggt ggcgcaggcg gcagcaacag cagtggcagc ggcgcggaag agaactccaa   15120
cgcggcagcc gcggcaatgc agccggtgga ggacatgaac gatcatgcca ttcgcggcga   15180 caccttgcc acacgggctg aggagaagcg cgctgaggcc gaagcagcgg ccgaagctgc   15240 cgccccgct gcgcaacccg aggtcgagaa gcctcagaag aaaccggtga tcaaacccct   15300
gacagaggac agcaagaaac gcagttacaa cctaataagc aatgacagca ccttcaccca   15360
gtaccgcagc tggtaccttg catacaacta cggcgaccct cagaccggaa tccgctcatg   15420
gaccctgctt tgcactcctg acgtaacctg cggctcggag caggtctact ggtcgttgcc   15480
agacatgatg caagaccccg tgaccttccg ctccacgcgc cagatcagca ctttccggt    15540
```

```
ggtgggcgcc gagctgttgc ccgtgcactc caagagcttc tacaacgacc aggccgtcta   15600
ctcccaactc atccgccagt ttacctctct gacccacgtg ttcaatcgct ttcccgagaa   15660
ccagattttg gcgcgcccgc cagccccccac catcaccacc gtcagtgaaa acgttcctgc   15720
tctcacagat cacgggacgc taccgctgcg caacagcatc ggaggagtcc agcgagtgac   15780
cattactgac gccagacgcc gcacctgccc ctacgtttac aaggccctgg catagtctc    15840 gccgcgcgtc ctatcgagcc gcactttttg agcaagcatg tccatcctta tatcgcccag   15900
caataacaca ggctggggcc tgcgcttccc aagcaagatg tttggcgggg ccaagaagcg   15960
ctccgaccaa cacccagtgc gcgtgcgcgg cactaccgc gcgccctggg gcgcgcacaa    16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
ggtgcgcgga gcccggcgct atgctaaaat gaagagacgg cggaggcgcg tagcacgtcg   16200
ccaccgccgc cgaccggca ctgccgccca acgcgcggcg gcgcgccctgc ttaaccgcgc   16260 acgtcgcacc ggccgacggg cggccatgcg ggccgctcga aggctggccg cgggtattgt   16320
cactgtgccc cccaggtcca ggcgacgagc ggccgccgca gcagccgcgg ccattagtgc   16380
tatgactcag ggtcgcaggg gcaacgtgta ttgggtgcgc gactcggtta gcggcctgcg   16440
cgtgcccgtg cgcacccgcc ccccgcgcaa ctagattgca agaaaaaact acttagactc   16500
gtactgttgt atgtatccag cggcggcggc gcgcaacgaa gctatgtcca agcgcaaaat   16560
caaagaagag atgctccagg tcatcgcgcc ggagatctat ggcccccccga agaaggaaga   16620 gcaggattac aagcccgaa agctaaagcg ggtcaaaaag aaaaagaaag atgatgatga    16680
tgaacttgac gacgaggtgg aactgctgca cgctaccgcg cccaggcgac gggtacagtg   16740
gaaaggtcga cgcgtaaaac gtgttttgcg accggcacc accgtagtct ttacgcccgg    16800
tgagcgctcc acccgcacct acaagcgcgt gtatgatgag gtgtacggcg acgaggacct   16860
gcttgagcag gccaacgagc gcctcgggga gtttgcctac ggaaagcggc ataaggacat   16920
gctggcgttg ccgctggacg agggcaaccc aacacctagc ctaaagcccg taacactgca   16980
gcaggtgctg cccgcgcttg caccgtccga agaaaagcgc ggcctaaagc gcgagtctgg   17040
tgacttggca cccaccgtgc agctgatggt acccaagcgc cagcgactgg aagatgtctt   17100
ggaaaaaatg accgtggaac ctgggctgga gcccgaggtc cgcgtgcggc caatcaagca   17160
ggtggcgccg ggactgggcg tgcagaccgt ggacgttcag atacccacta ccagtagcac   17220
cagtattgcc accgccacag agggcatgga gacacaaacg tccccggttg cctcagcggt   17280
ggcggatgcc gcggtgcagg cggtcgctgc ggccgcgtcc aagacctcta cggaggtgca   17340
aacgaccccg tggatgtttc gcgtttcagc ccccgcgc ccgcgcggtt cgaggaagta    17400
cggcgccgcc agcgcgctac tgcccgaata tgccctacat ccttccattg cgcctacccc   17460
cggctatcgt ggctacacct accgcccag aagacgagca actacccgac gccgaaccac    17520
cactggaacc cgccgccgcc gtcgccgtcg ccagcccgtg ctggccccga tttccgtgcg   17580
cagggtggct cgcgaaggag gcaggaccct ggtgctgcca acagcgcgct accacccccag   17640 catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg gcgccgtgcc   17880
```

```
cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc aacaaaagg     18240 tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctccct cgtacgagga ggcactaaag caaggcctgc    18480
ccaccacccg tcccatcgcg cccatggcta ccggagtgct gggccagcac acacccgtaa    18540
cgctggacct gcctccccc gccgacaccc agcagaaacc tgtgctgcca ggcccgaccg    18600
ccgttgttgt aacccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgctttccaa    18840
gatggctacc ccttcgatga tgccgcagtg gtcttacatg cacatctcgg gccaggacgc    18900
ctcggagtac ctgagccccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcaccctag ctgtgggtga taaccgtgtg ctggacatgg cttccacgta    19140 cttgacatc cgcggcgtgc tggacagggg ccctactttt aagccctact ctggcactgc    19200
ctacaacgcc ctggctccca agggtgcccc aaatccttgc gaatgggatg aagctgctac    19260
tgctcttgaa ataaacctag aagaagagga cgatgacaac gaagacgaag tagacgagca    19320
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc    19500
tgggagagtc cttaaaaaga ctaccccaat gaaaccatgt acggttcat atgcaaaacc    19560 cacaaatgaa aatggagggc aaggcattct tgtaaagcaa caaaatggaa agctagaaag    19620
tcaagtggaa atgcaatttt ctcaactac tgaggcgacc gcaggcaatg gtgataactt    19680
gactcctaaa gtggtattgt acagtgaaga tgtagatata gaaacccag acactctat     19740 ttcttacatg cccactatta aggaaggtaa ctcacgagaa ctaatgggcc aacaatctat    19800
gcccaacagg cctaattaca ttgcttttag ggacaatttt attggtctaa tgtattacaa    19860
cagcacgggt aatatgggtg ttctggcggg ccaagcatcg cagttgaatg ctgttgtaga    19920
tttgcaagac agaaacacag agctttcata ccagcttttg cttgattcca ttggtgatag    19980
aaccaggtac ttttctatgt ggaatcaggc tgttgacagc tatgatccag atgttagaat    20040
tattgaaaat catggaactg aagatgaact tccaaattac tgctttccac tgggaggtgt    20100
gattaataca gagactctta ccaaggtaaa acctaaaaca ggtcaggaaa atggatggga    20160
aaaagatgct acagaatttt cagataaaaa tgaaataaga gttggaaata attttgccat    20220
ggaaatcaat ctaaatgcca acctgtggag aaatttcctg tactccaaca tagcgctgta    20280
```

```
tttgcccgac aagctaaagt acagtccttc caacgtaaaa atttctgata acccaaacac   20340
ctacgactac atgaacaagc gagtggtggc tcccggytta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc taccctatac ccgccaacgc   20820
taccaacgtg cccatatcca tccctcccg caactgggcg gctttccgcg gctgggcctt    20880
cacgcgcctt aagactaagg aaaccccatc actgggctcg gctacgacc cttattacac    20940 ctactctggc tctataccct acctagatgg aaccttttac ctcaaccaca cctttaagaa   21000
ggtggccatt accttgact cttctgtcag ctggcctggc aatgaccgcc tgcttacccc    21060
caacgagttt gaaattaagc gctcagttga cggggagggt tacaacgttg cccagtgtaa    21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaactttat   21480
gtccatgggc gcactcacag acctgggcca aaaccttctc tacgccaact ccgcccacgc   21540
gctagacatg acttttgagg tggatcccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat attttttggg cacctatgac aagcgctttc caggctttgt ttctccacac   21840
aagctcgcct gcgccatagt caatacggcc ggtcgcgaga ctggggcgt acactggatg    21900 gcctttgcct ggaacccgca ctcaaaaaca tgctacctct ttgagccctt tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca caccccacc atgaaccta ttaccggggt acccaactcc     22200
atgctcaaca gtccccaggt acagccacc ctgcgtcgca accaggaaca gctctacagc    22260
ttcctggagc gccactcgcc ctacttccgc agccacagtg cgcagattag gagcgccact   22320 tcttttttgtc acttgaaaaa catgtaaaaa taatgtacta gagacacttt caataaaggc   22380
aaatgctttt atttgtacac tctcgggtga ttatttaccc ccaccttgc cgtctgcgcc    22440 gtttaaaaat caagggggtt ctgccgcgca tcgctatgcg ccactggcag ggacacgttg   22500
cgatactggt gttagtgct ccacttaaac tcaggcacaa ccatccgcgg cagctcggtg    22560
aagttttcac tccacaggct gcgcaccatc accaacgcgt ttagcaggtc gggcgccgat   22620
```

```
atcttgaagt cgcagttggg gcctccgccc tgcgcgcgcg agttgcgata cacagggttg    22680
cagcactgga acactatcag cgccgggtgg tgcacgctgg ccagcacgct cttgtcggag    22740
atcagatccg cgtccaggtc ctccgcgttg ctcagggcga acggagtcaa ctttggtagc    22800
tgccttccca aaaagggcgc gtgcccaggc tttgagttgc actcgcaccg tagtggcatc    22860
aaaaggtgac cgtgcccggt ctgggcgtta ggatacagcg cctgcataaa agccttgatc    22920
tgcttaaaag ccacctgagc cttttgcgcct tcagagaaga acatgccgca agacttgccg   22980
gaaaactgat tggccggaca ggccgcgtcg tgcacgcagc accttgcgtc ggtgttggag    23040
atctgcacca catttcggcc ccaccggttc ttcacgatct tggccttgct agactgctcc    23100
ttcagcgcgc gctgcccgtt ttcgctcgtc acatccattt caatcacgtg ctccttattt    23160
atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
tacgcctgca ggaatcgccc catcatcgtc acaaaggtct tgttgctggt gaaggtcagc    23340
tgcaacccgc ggtgctcctc gttcagccag gtcttgcata cggccgccag agcttccact    23400
tggtcaggca gtagtttgaa gttcgccttt agatcgttat ccacgtggta cttgtccatc    23460
agcgcgcgcg cagcctccat gcccttctcc cacgcagaca cgatcggcac actcagcggg    23520
ttcatcaccg taatttcact ttccgcttcg ctgggctctt cctcttcctc ttgcgtccgc    23580
ataccacgcg ccactgggtc gtcttcattc agccgccgca ctgtgcgctt acctcctttg    23640
ccatgcttga ttagcaccgg tgggttgctg aaacccacca tttgtagcgc cacatcttct    23700
ctttcttcct cgctgtccac gattacctct ggtgatggcg ggcgctcggg cttgggagaa    23760
gggcgcttct ttttcttctt gggcgcaatg gccaaatccg ccgccgaggt cgatggccgc    23820
gggctgggtg tgcgcggcac cagcgcgtct tgtgatgagt cttcctcgtc ctcggactcg    23880
atacgccgcc tcatccgctt ttttgggggc gcccggggag gcggcggcga cggggacggg    23940
gacgacacgt cctccatggt tgggggacgt gcgccgcac cgcgtccgcg ctcggggtg     24000 gtttcgcgct gctcctcttc ccgactggcc atttccttct cctataggca gaaaaagatc    24060
atggagtcag tcgagaagaa ggacagccta accgccccct ctgagttcgc caccaccgcc    24120
tccaccgatg ccgccaacgc gcctaccacc ttccccgtcg aggcacccccc gcttgaggag   24180 gaggaagtga ttatcgagca ggacccaggt tttgtaagcg aagacgacga ggaccgctca    24240
gtaccaacag aggataaaaa gcaagaccag gacaacgcag aggcaaacga ggaacaagtc    24300
gggcgggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatcttttt tccaaaactg caagataccc    24600
ctatcctgcc gtgccaaccg cagccgagcg acaagcagc tggccttgcg gcagggcgct    24660 gtcataccctg atatcgcctc gctcaacgaa gtgccaaaaa tctttgaggg tcttggacgc    24720
gacgagaagc gcgcggcaaa cgctctgcaa caggaaaaca gcgaaaatga agtcactct    24780 ggagtgttgg tggaactcga gggtgacaac gcgcgcctag ccgtactaaa acgcagcatc    24840
gaggtcaccc actttgccta cccggcactt aacctacccc caaggtcat gagcacagtc     24900 atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
```

-continued

```
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcattttccc cgaacgcctg    25500
cttaaaaccc tgcaacaggg tctgccagac ttcaccagtc aaagcatgtt gcagaacttt    25560
aggaacttta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct ttgagctgca gggtccctcg    25860
cctgacgaaa agtccgcggc tccggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacgggggg    26100 gtttacttgg accccagtc cggcgaggag ctcaacccaa tcccccgcc gccgcagccc    26160 tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
gaaatcggca accggttcca gcatggctac aacctccgct cctcaggcgc cgccggcact    26460
gcccgttcgc cgacccaacc gtagatggga caccactgga accagggccg gtaagtccaa    26520
gcagccgccg ccgttagccc aagagcaaca acagcgccaa ggctaccgct catggcgcgg    26580
gcacaagaac gccatagttg cttgcttgca agactgtggg ggcaacatct ccttcgcccg    26640
ccgctttctt ctctaccatc acggcgtggc cttcccccgt aacatcctgc attactaccg    26700
tcatctctac agcccatact gcaccggcgg cagcggcagc ggcagcaaca gcagcggcca    26760
cacagaagca aaggcgaccg gatagcaaga ctctgacaaa gcccaagaaa tccacagcgg    26820
cggcagcagc aggaggagga gcgctgccgtc tggcgcccaa cgaacccgta tcgacccgcg    26880
agcttagaaa caggattttt cccactctgt atgctatatt tcaacagagc aggggccaag    26940
aacaagagct gaaaataaaa aacaggtctc tgcgatccct caccccgcagc tgcctgtatc    27000 acaaaagcga agatcagctt cggcgcacgc tggaagacgc ggaggctctc ttcagtaaat    27060
actgcgcgct gactcttaag gactagtttc gcgcccttc tcaaatttaa gcgcgaaaac    27120
tacgtcatct ccagcggcca cacccggcgc cagcacctgt cgtcagcgcc attatgagca    27180
aggaaattcc cacgccctac atgtggagtt accagccaca aatgggactt gcggctggag    27240
ctgcccaaga ctactcaacc cgaataaact acatgagcgc gggaccccac atgatatccc    27300
gggtcaacgg aatccgcgcc caccgaaacc gaattctctt ggaacaggcg gctattacca    27360
```

```
ccacacctcg taataacctt aatccccgta gttggcccgc tgccctggtg taccaggaaa   27420
gtcccgctcc caccactgtg gtacttccca gagacgccca ggccgaagtt cagatgacta   27480
actcaggggc gcagcttgcg ggcggctttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctgaggca   27720 ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggcccggcgc acggcgtccg gcttaccgcc cagggagagc   28020
ttgcccgtag cctgattcgg gagtttaccc agcgcccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260 ggtacttta acatctctcc ctctgtgatt tacaacagtt tcaacccaga cggagtgagt   28320
ctacgagaga acctctccga gctcagctac tccatcagaa aaaacaccac cctccttacc   28380
tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500
aaaaccctta gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcatttatt gtcagctttt taaacgctgg ggtcgccacc caagatgatt   28740
aggtacataa tcctaggttt actcacccct tgcgtcagcc cacggtaccac ccaaaaggtg   28800 gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aacttttatg tatactttc cattttatga aatgtgcgac   29040
attaccatgt acatgagcaa acagtataag ttgtggcccc cacaaaattg tgtgaaaaac   29100
actggcactt tctgctgcac tgctatgcta attacagtgc tcgctttggt ctgtaccta   29160 ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtcccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttctttct   29760
```

```
cttacagtat gattaaatga gacatgattc ctcgagtttt tatattactg acccttgttg    29820
cgcttttttg tgcgtgctcc acattggctg cggtttctca catcgaagta gactgcattc    29880
cagccttcac agtctatttg ctttacggat ttgtcaccct cacgctcatc tgcagcctca    29940
tcactgtggt catcgccttt atccagtgca ttgactgggc tgtgtgcgc tttgcatatc     30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc ccaccccac    30420
tgaaatcagc tactttaatc taacaggagg agatgactga caccctagat ctagaaatgg    30480
acggaattat tacagagcag cgcctgctag aaagacgcag ggcagcggcc gagcaacagc    30540
gcatgaatca agagctccaa gacatggtta acttgcacca gtgcaaaagg ggtatctttt    30600
gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840
aaaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gtttcctcct gttcctgtcc atccgcaccc    31020
actatcttca tgttgttgca gatgaagcgc gcaagaccgt ctgaagatac cttcaacccc    31080
gtgtatccat atgacacgga aaccggtcct ccaactgtgc ctttttcttac tcctccettt    31140
gtatccccca atgggtttca agagagtccc cctggggtac tctctttgcg cctatccgaa    31200
cctctagtta cctccaatgg catgcttgcg ctcaaaatgg gcaacggcct ctctctggac    31260
gaggccggca accttacctc ccaaaatgta accactgtga gcccacctct caaaaaaacc    31320
aagtcaaaca taaacctgga aatatctgca cccctcacag ttacctcaga agccctaact    31380
gtggctgccg ccgcacctct aatggtcgcg ggcaacacac tcaccatgca atcacaggcc    31440
ccgctaaccg tgcacgactc caaacttagc attgccaccc aaggacccct cacagtgtca    31500
gaaggaaagc tagccctgca acatcaggc cccctcacca ccaccgatag cagtacccctt    31560
actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaacagac gccttatact tgatgttagt    31860
tatccgtttg atgctcaaaa ccaactaaat ctaagactag acagggccc tctttttata    31920
aactcagccc acaacttgga tattaactac aacaaggcc tttacttgtt tacagcttca    31980
aacaattcca aaagcttga ggttaaccta agcactgcca aggggttgat gtttgacgct    32040
acagccatag ccattaatgc aggagatggg cttgaatttg gttcacctaa tgcaccaaac    32100
```

```
acaaatcccc tcaaaacaaa aattggccat ggcctagaat ttgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700
tttcatgggg actggtctgg ccacaactac attaatgaaa tatttgccac atcctcttac    32760
actttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcaccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctcttttgg catgttgtaa ttcaccacct cccggtacca    33600
tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgtttttt ttttattcca aaagattatc caaaacctca    34380
aaatgaagat ctattaagtg aacgcgctcc cctccggtgg cgtggtcaaa ctctacagcc    34440
aaagaacaga taatggcatt tgtaagatgt tgcacaatgg cttccaaaag gcaaacggcc    34500
```

```
ctcacgtcca agtggacgta aaggctaaac ccttcagggt gaatctcctc tataaacatt    34560
ccagcacctt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttcccccg ccaggaacca    34860 tgacaaaaga acccacactg attatgacac gcatactcgg agctatgcta accagcgtag    34920
ccccgatgta agcttgttgc atgggcggcg atataaatg caaggtgctg ctcaaaaaat    34980
caggcaaagc ctcgcgcaaa aagaaagca catcgtagtc atgctcatgc agataaaggc    35040
aggtaagctc cggaaccacc acagaaaaag acaccatttt tctctcaaac atgtctgcgg    35100
gtttctgcat aaacacaaaa taaaataaca aaaaacatt taaacattag aagcctgtct    35160
tacaacagga aaaacaaccc ttataagcat aagacggact acggccatgc cggcgtgacc    35220
gtaaaaaaac tggtcaccgt gattaaaaag caccaccgac agctcctcgg tcatgtccgg    35280
agtcataatg taagactcgg taaacacatc aggttgattc acatcggtca gtgctaaaaa    35340
gcgaccgaaa tagcccgggg gaatacatac ccgcaggcgt agagacaaca ttacagcccc    35400
cataggaggt ataacaaaat taataggaga gaaaaacaca taaacacctg aaaaaccctc    35460
ctgcctaggc aaaatagcac cctcccgctc cagaacaaca tacagcgctt ccacagcggc    35520
agccataaca gtcagcctta ccagtaaaaa agaaaaccta ttaaaaaaac accactcgac    35580
acggcaccag ctcaatcagt cacagtgtaa aaaagggcca agtgcagagc gagtatatat    35640
aggactaaaa aatgacgtaa cggttaaagt ccacaaaaaa cacccagaaa accgcacgcg    35700
aacctacgcc cagaaacgaa agccaaaaaa cccacaactt cctcaaatcg tcacttccgt    35760
tttcccacgt tacgtaactt cccattttaa gaaaactaca attcccaaca catacaagtt    35820
actccgccct aaaacctacg tcacccgccc cgttcccacg ccccgcgcca cgtcacaaac    35880
tccaccccct cattatcata ttggcttcaa tccaaaataa ggtatattat tgatgatg     35938
```

<210> SEQ ID NO 53
<211> LENGTH: 10
<212> TYPE: PRT
<213> ORGANISM: Homo sapiens

<400> SEQUENCE: 53

Ser Asn Thr Lys Val Asp Lys Lys Val Glu
1               5                   10

<210> SEQ ID NO 54
<211> LENGTH: 8
<212> TYPE: PRT
<213> ORGANISM: Homo sapiens

<400> SEQUENCE: 54

Thr Lys Val Asp Lys Arg Val Glu
1               5

<210> SEQ ID NO 55
<211> LENGTH: 470
<212> TYPE: PRT
<213> ORGANISM: Artificial Sequence
<220> FEATURE:
<223> OTHER INFORMATION: Synthetic -continued

```
<400> SEQUENCE: 55

Met Leu Pro Cys Leu Val Val Leu Ala Leu Leu Ser Leu Arg
1               5                   10                  15

Leu Gly Ser Asp Ala His Gly Thr Glu Leu Pro Ser Pro Ser Val
                20                  25                  30

Trp Phe Glu Ala Glu Phe Phe His Ile Leu His Trp Thr Pro Ile
                35                  40                  45

Pro Asn Gln Ser Glu Ser Thr Cys Tyr Glu Val Ala Leu Leu Arg Tyr
            50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
                115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Ile
210                 215                 220

Ser Leu Thr Arg Gln Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

```
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 56
<211> LENGTH: 468
<212> TYPE: PRT
<213> ORGANISM: Artificial Sequence
<220> FEATURE:
<223> OTHER INFORMATION: Synthetic

<400> SEQUENCE: 56

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300
```

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
        340                 345                 350

Ile Glu Lys Thr Ile Ser Lys Ala Lys Gly Gln Pro Arg Glu Pro Gln
    355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465

<210> SEQ ID NO 57
<211> LENGTH: 16
<212> TYPE: PRT
<213> ORGANISM: Homo sapiens

<400> SEQUENCE: 57

Asn Val Asn His Lys Pro Ser Asn Thr Lys Val Asp Lys Arg Val Glu
1               5                   10                  15

<210> SEQ ID NO 58
<211> LENGTH: 476
<212> TYPE: PRT
<213> ORGANISM: Artificial Sequence
<220> FEATURE:
<223> OTHER INFORMATION: Synthetic

<400> SEQUENCE: 58

Met Leu Pro Cys Leu Val Val Leu Ala Ala Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
210                 215                 220

Ser Leu Thr Arg Gln Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 59
<211> LENGTH: 14
<212> TYPE: PRT
<213> ORGANISM: Homo sapiens

<400> SEQUENCE: 59

Asn His Lys Pro Ser Asn Thr Lys Val Asp Lys Arg Val Glu
1               5                   10

<210> SEQ ID NO 60

```
<211> LENGTH: 12
<212> TYPE: PRT
<213> ORGANISM: Homo sapiens

<400> SEQUENCE: 60

Lys Pro Ser Asn Thr Lys Val Asp Lys Arg Val Glu
1               5                   10

<210> SEQ ID NO 61
<211> LENGTH: 10
<212> TYPE: PRT
<213> ORGANISM: Homo sapiens

<400> SEQUENCE: 61

Ser Asn Thr Lys Val Asp Lys Arg Val Glu
1               5                   10

<210> SEQ ID NO 62
<211> LENGTH: 16
<212> TYPE: PRT
<213> ORGANISM: Homo sapiens

<400> SEQUENCE: 62

Asn Val Asn His Lys Pro Ser Asn Thr Lys Val Asp Lys Lys Val Glu
1               5                   10                  15

<210> SEQ ID NO 63
<211> LENGTH: 14
<212> TYPE: PRT
<213> ORGANISM: Homo sapiens

<400> SEQUENCE: 63

Asn His Lys Pro Ser Asn Thr Lys Val Asp Lys Lys Val Glu
1               5                   10

<210> SEQ ID NO 64
<211> LENGTH: 8
<212> TYPE: PRT
<213> ORGANISM: Homo sapiens

<400> SEQUENCE: 64

Thr Lys Val Asp Lys Lys Val Glu
1               5
```